(12) United States Patent
Chen et al.

(10) Patent No.: US 12,305,233 B1
(45) Date of Patent: May 20, 2025

(54) ULTRA-HIGH-THROUGHPUT ASSAY FOR TELOMERASE REPEAT ADDITION PROCESSIVITY

(71) Applicant: ARIZONA BOARD OF REGENTS ON BEHALF OF ARIZONA STATE UNIVERSITY, Scottsdale, AZ (US)

(72) Inventors: Julian Chen, Chandler, AZ (US); Yang Li, Chandler, AZ (US)

(73) Assignee: Arizona Board of Regents on Behalf of Arizona, Scottsdale, AZ (US)

( * ) Notice: Subject to any disclaimer, the term of this patent is extended or adjusted under 35 U.S.C. 154(b) by 491 days.

(21) Appl. No.: 17/372,255

(22) Filed: Jul. 9, 2021

Related U.S. Application Data

(60) Provisional application No. 63/050,095, filed on Jul. 9, 2020.

(51) Int. Cl.
*C12Q 1/6876* (2018.01)

(52) U.S. Cl.
CPC ................... *C12Q 1/6876* (2013.01)

(58) Field of Classification Search
None
See application file for complete search history.

(56) References Cited

U.S. PATENT DOCUMENTS

| | | | | |
|---|---|---|---|---|
| 5,693,474 | A * | 12/1997 | Shay | C12Q 1/6886 436/63 |
| 5,891,639 | A | 4/1999 | Harley | |
| 8,234,080 | B2 | 7/2012 | Skordalakes | |
| 8,374,838 | B2 | 2/2013 | Skordalakes | |
| 8,481,721 | B2 | 7/2013 | Harley | |
| 8,609,736 | B2 | 12/2013 | Gazit | |
| 8,759,304 | B2 | 6/2014 | Harley | |
| 9,234,230 | B2 | 1/2016 | Skordalakes | |
| 2001/0039039 | A1 * | 11/2001 | Weissman | C12Q 1/6827 435/6.12 |
| 2009/0269771 | A1 * | 10/2009 | Schroeder | C12Q 1/6827 435/6.12 |
| 2014/0134610 | A1 * | 5/2014 | Pham | C12Q 1/6855 435/6.1 |
| 2014/0296081 | A1 * | 10/2014 | Diehn | C12Q 1/6827 506/8 |
| 2018/0051277 | A1 * | 2/2018 | Godfrey | C12Q 1/686 |

FOREIGN PATENT DOCUMENTS

| | | |
|---|---|---|
| CN | 1298951 A | 6/2001 |
| KR | 20030058023 A | 7/2003 |

OTHER PUBLICATIONS

Tomlinson (Methods 114 (2017) 85-95).*
Van Dijk (Trends in Genetics Sep. 2018 vol. 34 No. 9 pp. 666-680).*
Wu RA, et al. (2017b) Telomerase mechanism of telomere synthesis. Annu Rev Biochem 86: 439-460.
Wyatt HDM, et al. (2007) Characterization of physical and functional anchor site interactions in human telomerase. Mol Cell Biol 27: 3226-3240.
Xie M, et al. (2010) A novel motif in telomerase reverse transcriptase regulates telomere repeat addition rate and processivity. Nucleic Acids Res 38: 1982-1996.
Yang G, et al. (2002) Correlation of the kinetics of finger domain mutants in R869 DNA polymerase with its structure. Biochemistry 41: 2526-2534.
Yang W, et al. (2015) A DNA-hairpin model for repeat-addition processivity in telomere synthesis. Nat Struct Mol Biol 22: 844-847.
Zaug AJ, et al. (2013) Many disease-associated variants of hTERT retain high telomerase enzymatic activity. Nucleic Acids Res 41: 8969-8978.
Zaug AJ, et al. (2008) Mutation in TERT separates processivity from anchor-site function. Nat Struct Mol Biol 15: 870-872.
Hammond PW, et al (1997) dGTP-dependent processivity and possible template switching of euplotes telomerase. Nucleic Acids Res 25: 3698-3704.
Akiyama BM, et al. (2015) The telomerase essential N-terminal domain promotes DNA synthesis by stabilizing short RNA-DNA hybrids. Nucleic Acids Res 43: 1-13.
Alder JK, et al. (2011) Ancestral mutation in telomerase causes defects in repeat addition processivity and manifests as familial pulmonary fibrosis. PLoS Genet 7: e1001352.
Armanios, M., et al. "The telomere syndromes." Nature Reviews Genetics 13.10 (2012): 693-704.
Arnoult N, et al. (2015) Complex interactions between the DNA-damage response and mammalian telomeres. Nat Struct Mol Biol 22: 859-866.
Autexier C, et al. (2006) The structure and function of telomerase reverse transcriptase. Annu Rev Biochem 75: 493-517.
Bradshaw PC, et al. (2005) A computational model of mitochondrial deoxynucleotide metabolism and DNA replication. Am J Physiol Cell Physiol 288: C989-C1002.
Brown AF, et al. (2014) A self-regulating template in human telomerase. Proc Natl Acad Sci USA 111: 11311-11316.
Chen J-L, et al. (2003a) Template boundary definition in mammalian telomerase. Genes Dev 17: 2747-2752.
Chen J-L, et al. (2003b) Determinants in mammalian telomerase RNA that mediate enzyme processivity and cross-species incompatibility. EMBO J 22: 304-314.
Chen, Y., et al. (2018). A single nucleotide incorporation step limits human telomerase repeat addition activity. EMBO. J. 37(6): e97953.
Collins K, et al. (1995) Utilization of ribonucleotides and RNA primers by Tetrahymena telomerase. EMBO J 14: 5422-5432.
Dokal, I. "A disease of premature ageing." The Lancet 358 (2001): S27.

(Continued)

*Primary Examiner* — Amanda Haney
(74) *Attorney, Agent, or Firm* — FULLER IP LAW LLC; Rodney J. Fuller

(57) ABSTRACT

The present invention provides methods and kits for determining telomerase processivity. These methods and kits may be used to screen for drugs that inhibit or enhance telomerase repeat addition activity, and are readily adapted to an ultra-high-throughput format.

11 Claims, 9 Drawing Sheets
Specification includes a Sequence Listing.

(56) References Cited

OTHER PUBLICATIONS

Drosopoulos WC, et al. (2005) Human telomerase RNA template sequence is a determinant of telomere repeat extension rate. J Biol Chem 280: 32801-32810.
Drosopoulos WC, et al. (2010) The telomerase-specific T motif is a restrictive determinant of repetitive reverse transcription by human telomerase. Mol Cell Biol 30: 447-459.
Finger SN, et al. (2008) Multiple DNA-binding sites in Tetrahymena telomerase. Nucleic Acids Res 36: 1260-1272.
Garforth SJ, et al. (2008) Utilization of a deoxynucleoside diphosphate substrate by HIV reverse transcriptase. PLoS One 3: e2074.
Gilley D, et al. (1996) Specific RNA residue interactions required for enzymatic functions of Tetrahymena telomerase. Mol Cell Biol 16: 66-75.
Gilley D, et al. (1995) Altering specific telomerase RNA template residues affects active site function. Genes Dev 9: 2214-2226.
Gramatges MM, et al. (2013) A homozygous telomerase T-motif variant resulting in markedly reduced repeat addition processivity in siblings with Hoyeraal Hreidarsson syndrome. Blood 121: 3586-3593.
Greider CW (1991) Telomerase is processive. Mol Cell Biol 11: 4572-4580.
Hardy CD, et al. (2001) Requirements for the dGTP-dependent repeat addition processivity of recombinant Tetrahymena telomerase. J Biol Chem 276: 4863-4871.
Hockemeyer D, et al. (2015) Control of telomerase action at human telomeres. Nat Struct Mol Biol 22: 848-852.
Huard S, et al. (2003) The C terminus of the human telomerase reverse transcriptase is a determinant of enzyme processivity. Nucleic Acids Res 31: 4059-4070.
Hwang H, et al. (2014) Single-molecule real-time detection of telomerase extension activity. Sci Rep 4: 6391.
Jacobs SA, et al. (2006) Crystal structure of the essential N-terminal domain of telomerase reverse transcriptase. Nat Struct Mol Biol 13: 218-225.
Jansson LI, et al. (2015) Structural basis of template-boundary definition in Tetrahymena telomerase. Nat Struct Mol Biol 22: 883-888.
Jiang J, et al. (2015) Structure of Tetrahymena telomerase reveals previously unknown subunits, functions, and Interactions. Science 350: aab4070.
Kornberg A (1957) Pathways of enzymatic synthesis of nucleotides and polynucleotides. In The chemical basis of heredity, McElroy WD, Glass B (eds), pp. 579-608. Baltimore: The Johns Hopkins Press.
Kornberg A (1969) Active center of DNA polymerase. Science 163: 1410-1418.
Latrick CM, et al. (2010) POT1-TPP1 enhances telomerase processivity by slowing primer dissociation and aiding translocation. EMBO J 29: 924-933.
Lee MS, et al. (1993) Sequence-specific DNA primer effects on telomerase polymerization activity. Mol Cell Biol 13: 6586-6599.
Lingner J, et al. (1997) Reverse transcriptase motifs in the catalytic subunit of telomerase. Science 276: 561-567.
Lue NF, et al. (2003) A conserved telomerase motif within the catalytic domain of telomerase reverse transcriptase is specifically required for repeat addition processivity. Mol Cell Biol 23: 8440-8449.
Maine IP, et al. (1999) Effect of dGTP concentration on human and CHO telomerase. Biochemistry 38: 15325-15332.
Mitchell M, et al. (2010) Structural basis for telomerase catalytic subunit TERT binding to RNA template and telomeric DNA. Nat Struct Mol Biol 17: 513-518.
Parks JW, et al. (2017) Single-molecule FRET-Rosetta reveals RNA structural rearrangements during human telomerase catalysis. RNA 23: 175-188.
Parks JW, et al. (2014) Coordinated DNA dynamics during the human telomerase catalytic cycle. Nat Commun 5: 4146.
Podlevsky JD, et al. (2012) It all comes together at the ends: telomerase structure, function, and biogenesis. Mutation Res 730: 3-11.
Podlevsky JD, et al. (2016) Evolutionary perspectives of telomerase RNA structure and function. RNA Biol 13: 720-732.
Qi X, et al. (2013) The common ancestral core of vertebrate and fungal telomerase RNAs. Nucleic Acids Res 41: 450-462.
Qi X, et al. (2012) RNA/DNA hybrid binding affinity determines telomerase template-translocation efficiency. EMBO J 31: 150-161.
Robart AR, et al. (2010) Investigation of human telomerase holoenzyme assembly, activity, and processivity using disease-linked subunit variants. J Biol Chem 285: 4375-4386.
Schmidt JC, et al. (2015) Human telomerase: biogenesis, trafficking, recruitment, and activation. Genes Dev 29: 1095-1105.
Seto AG, et al. (2003) A template-proximal RNA paired element contributes to *Saccharomyces cerevisiae* telomerase activity. RNA 9: 1323-1332.
Sfeir AJ, et al. (2005) Telomere-end processing: the terminal nucleotides of human chromosomes. Mol Cell 18: 131-138.
Sun D, et al. (1999) Regulation of catalytic activity and processivity of human telomerase. Biochemistry 38: 4037-4044.
Tomlinson CG, et al. (2015) Two-step mechanism involving active-site conformational changes regulates human telomerase DNA binding. Biochem J 465: 347-357.
Tzfati Y, et al. (2000) Template boundary in a yeast telomerase specified by RNA structure. Science 288: 863-867.
Watson, J. D. "Origin of concatemeric T7DNA." Nature New Biology 239.94 (1972): 197-201.
Wu RA, et al. (2017a) DNA-binding determinants and cellular thresholds for human telomerase repeat addition processivity. EMBO J 36: 1908-1927.

* cited by examiner

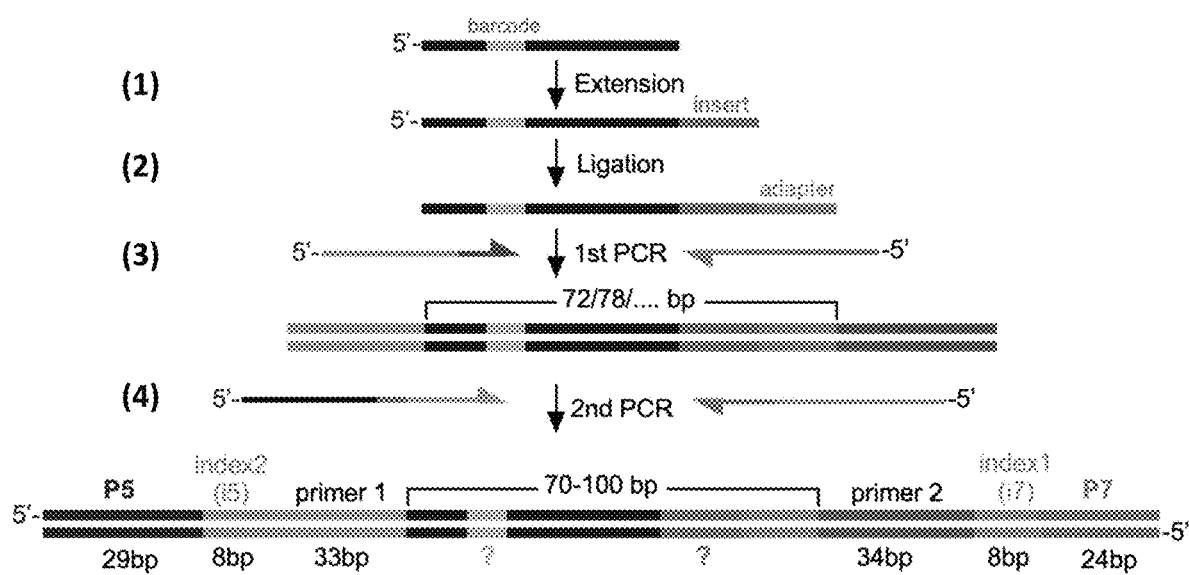

Fig. 6
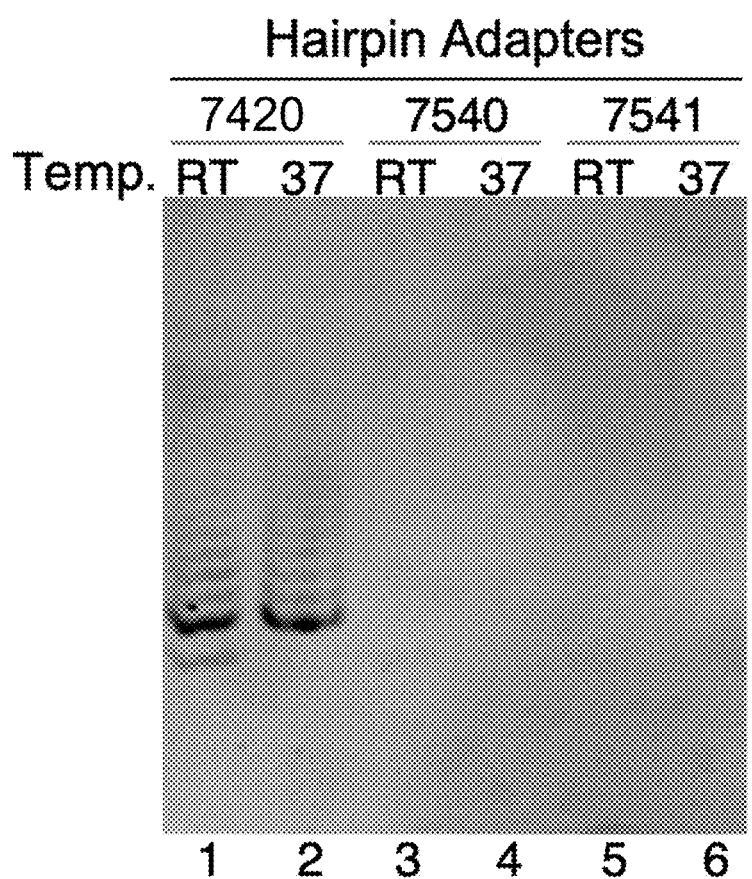
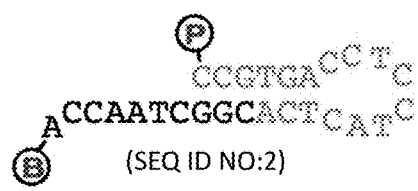
ASU-7420
(SEQ ID NO:2)
ASU-7540
(SEQ ID NO:3)
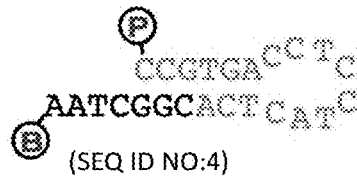
ASU-7541
(SEQ ID NO:4)

ULTRA-HIGH-THROUGHPUT ASSAY FOR TELOMERASE REPEAT ADDITION PROCESSIVITY

CROSS-REFERENCE TO RELATED APPLICATIONS

This application claims priority to U.S. Provisional Application No. 63/050,095 filed on Jul. 9, 2020, the contents of which are incorporated by reference in their entireties.

STATEMENT REGARDING FEDERALLY SPONSORED RESEARCH

This invention was made with government support under Grant Number R01 GM094450 awarded by the National Institutes of Health. The government has certain rights in this invention.

SEQUENCE LISTING

A Sequence Listing accompanies this application and is submitted as an ASCII text file of the sequence listing named "112624_01277_ST25.txt" which is 2,727 bytes in size and was created on Jul. 6, 2021. The sequence listing is electronically submitted via EFS-Web with the application and is incorporated herein by reference in its entirety.

BACKGROUND

An effective anti-aging drug will have enormous values in medicine and the healthcare market. By 2030, 1 in 5 Americans is projected to be over 65 years old. More than 90% of adults over age 65 experience one or more chronic conditions and require medical care, which is a daunting challenge to the healthcare system. One of the solutions to this pressing societal problem is to promote healthy and resilient aging through innovative physiological interventions at the molecular and cellular levels. Moreover, the size of the global anti-aging market is over 50 billion dollars annually, indicating a great need for effective products.

Telomere shortening is involved in all aspects of the aging process on a cellular level. Telomeres are specialized nucleoprotein structures that protect the ends of chromosomes from end-to-end fusions and are essential for maintaining genome integrity. The telomere sequences consist of tracts of tandemly repeated nucleotide sequences: $(TTAGGG)_n$. In human cells, the length of telomeres varies dramatically from 5 to 15 Kb, depending on the cellular age. However, the mechanisms that control telomere length are not well understood.

Telomere function and chromosome stability are essential for normal cell function and growth control. The telomere repeats serve as binding sites for specific proteins that distinguish the natural chromosome ends from DNA breaks. Telomeres are shortened with each round of DNA replication due to a phenomenon known as the "end-replication problem," which results from the inability of conventional DNA polymerase to fully replicate the 3'-end of a linear DNA molecule. In normal cells, telomere shortening and/or dysfunction can lead to chromosome fusions, cell senescence, and ultimately cell death. Thus, telomere length determines the replicative capacity of normal human cells and is viewed as a molecular clock that counts down as the cell ages. Remarkably, this cellular aging process can be stopped by ectopic expression of the enzyme telomerase.

Telomerase is the enzyme responsible for maintaining telomere length. Telomerase is a unique reverse transcriptase that specializes in telomeric DNA synthesis at chromosome ends. It contains two essential core components: the catalytic protein telomerase reverse transcriptase (TERT) and telomerase RNA (TR). The catalytic TERT protein synthesizes telomere DNA with a sequence specified by a short template sequence provided by the telomerase RNA component. This core ribonucleoprotein (RNP) complex associates with several accessory proteins, such as dyskerin, that play important roles in the biogenesis and regulation of the telomerase holoenzyme.

Telomerase is essential for maintaining cellular immortality in stem cells. Deficiency or reduction of telomerase activity in stem cells results in reduced self-renewal capacity and premature aging phenotypes. "Short-telomere" diseases, such as dyskeratosis congenita (DKC), aplastic anemia (AA), idiopathic pulmonary fibrosis (IPF), Hoyeraal-Hreidarsson syndrome, acute myelogenous leukemia, and familial liver cirrhosis have been genetically linked to mutations in genes that encode telomerase components or proteins that regulate telomerase activity and telomere length. The symptoms of these diseases gradually worsen in subsequent generations of families with these diseases because the telomere progressively become shorter with each generation.

DKC, for example, is an inherited disorder with clinical manifestations that include abnormal skin pigmentation, oral leukoplakia, and nail dystrophy. The majority of DKC associated deaths result from bone marrow failure, immunodeficiency, pulmonary complications, and malignancies. The autosomal dominant form of this disease is caused by mutations within the genes that encode TERT and TR. These mutations cause a reduction in telomerase activity, which results in a limited capacity for stem cell proliferation and low blood cell counts or anemia.

Thus, there is a need in the art for drugs that increase telomerase activity to provide both a means to delay the aging process and an effective cure for short-telomere diseases.

SUMMARY

In one aspect, the present invention provides methods for determining telomerase processivity. The methods comprise (a) incubating a telomerase, a telomeric DNA primer, and dNTPs comprising 5-100 M dGTP under suitable conditions for telomerase activity, optionally in the presence of an agent, thereby forming telomerase-extended DNA products; and (b) analyzing the telomerase-extended DNA products to determine the processivity of said telomerase.

In some embodiments, the methods further comprise ligating a hairpin adapter to the telomerase-extended DNA products produced in step (a) prior to step (b). The hairpin adapter used with the present invention comprises: (a) a sequence that is complementary to the 3' end of the telomerase-extended DNA products; (b) a 5' phosphate to allow for ligation with the telomerase-extended DNA products; (c) a purification moiety; and (d) PCR primer binding site.

In a second aspect, the present invention provides kits for performing the telomerase processivity assay disclosed herein. The kits comprise at least one telomeric DNA primer and dNTP mix comprising 5-100 M dGTP, 100-1000 μM dTTP, and 100-100 μM dATP.

BRIEF DESCRIPTION OF THE DRAWINGS

FIG. 1 shows a schematic overview of the ultra-high-throughput assay disclosed herein, which is designed to measure telomerase activity and processivity. In step (1), a telomeric DNA primer (dark blue) comprising a nucleotide barcode (lilac) is incubated with a telomerase and dNTPs under suitable conditions for telomerase activity, such that the telomerase adds DNA repeats (green; labeled insert) to the 3' end of the telomeric DNA primer, forming a telomerase-extended DNA product. In step (2), a hairpin adapter (orange; labeled adapter) is ligated to the 3' end of the telomerase-extended DNA product. In step (3), the ligated product is PCR amplified using primers that add sequencing adapters (yellow and pink) to its ends. In step (4), the amplified product is subjected to a second PCR amplification, in which primers are used to add Illumina index sequences (orange and light blue; labeled as index 2 (I5) and index 1 (i7), respectively) and P5/P7 sequences that will anneal to complementary oligonucleotides on the flowcell surface (black and gray), thereby generating a multiplexed DNA library for Illumina sequencing.

FIG. 6 shows a comparison of the ability of different hairpin adapters (ASU-7420 (SEQ ID NO: 2), ASU-7540 (SEQ ID NO:3), and ASU-7541 (SEQ ID NO:4)) to be ligated to telomerase-extended DNA products.

DETAILED DESCRIPTION

Figure 2A:
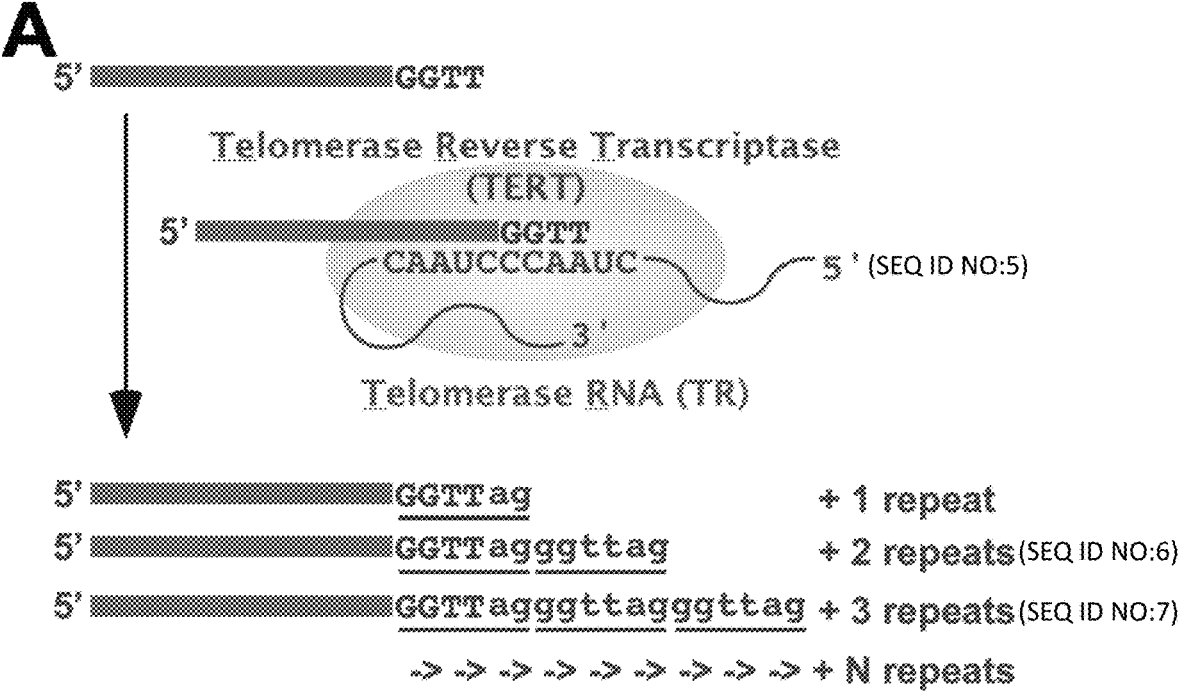
FIG. 2A shows a schematic of the telomerase primer-extension reaction. Telomerase consists of two core components, telomerase reverse transcriptase (TERT) and telomerase RNA (TR). The TERT protein catalyzes DNA synthesis to add telomeric DNA repeats (GGTTAG)n onto the DNA primer. The TR component provides the template for base pairing with the 3'-end of the DNA primer and synthesis of DNA repeats. Telomerase is processive and is capable of adding multiple repeats to the primer in a single reaction.

To address the need for treatments for short-telomere diseases and aging, the present inventors have developed a rapid screening method that can be used to identify small molecules or other agents that enhance the intrinsic activity of the telomerase enzyme or can be used to test for telomerase activity in a sample. This method allows telomerase repeat addition activity and processivity to be analyzed in an ultra-high-throughput manner. For example, in some embodiments, a different telomerase primer-extension reaction is performed in each well of a microplate to assess the ability of this enzyme to add DNA repeats to a telomeric DNA primer under a specific condition, such as in the presence of a small molecule or other agent, and assess the effect of the agent on telomerase activity or processivity. The telomerase-extended DNA products generated in each of the individual reactions are pooled and ligated to a hairpin adapter that is used to purify the telomerase-extended DNA products away from leftover telomeric DNA primer. The purified telomerase-extended DNA products are then PCR amplified to generate a DNA library, which is subjected to next-generation high-throughput DNA sequencing. The sequencing reads are analyzed to determine the number and length of DNA products synthesized in each well (FIG. 1). From this analysis, small molecules that enhance or inhibit telomerase processivity may be identified. Any processivity enhancing molecules can be evaluated as drugs to combat aging or treat patients with short-telomere diseases, while any telomerase inhibiting molecules can be evaluated as anti-cancer drugs.

The present invention offers several advantages. First, it is ultra-high-throughput. By using a bar-coding system and optimized telomerase primer-extension reaction conditions, this method will allow more than 500,000 small molecules to be screened in less than 6 months. Second, it is highly cost-effective, as it utilizes a secondary index system to allow DNA products from more than 30,000 reactions to be pooled and sequenced in a single next-generation sequencing reaction. Third, it identifies drugs that act on telomerase directly, reducing the likelihood of off-target, non-specific effects.

Importantly, the present invention allows one to screen for telomerase-interacting drugs that do not promote tumorigenesis in normal cells. In humans, telomerase is expressed in the germline and in stem cells, but not in normal somatic cells. Under normal circumstances, telomerase-negative cells only divide a limited number of times, referred to as the Hayflick limit, before they undergo senescence. The telomerase down-regulation and telomere shortening that occurs in normal human cells may be the result of a tumor suppressor mechanism that limits the growth potential of cancer cells. While it is repressed in most somatic cells, telomerase activity is abnormally upregulated in most human tumors or cancer cells, allowing for maintained chromosome stability and infinite growth. About 85% of malignant tumors tested exhibit telomerase activity. Thus, a drug that induces telomerase activity in telomerase-negative somatic cells may also increase the probability of tumor development. To address this complication, the inventors have designed their novel screening method to identify drugs that do not enhance tumorigenesis. In human tumor cells, telomerase activity is restored by activating expression of TERT mRNA and TERT protein. Thus, the inventors will screen for drugs that specifically enhance the activity of endogenous telomerase in stem cells and do not activate TERT protein expression in normal cells that lack telomerase. Because such drugs will not activate telomerase activity in normal cells, they will form safer anti-aging drugs than the telomerase activators currently on the market.

Methods:

The present invention provides methods for determining telomerase processivity. The methods comprise (a) incubating a telomerase, a telomeric DNA primer, and deoxyribonucleotide triphosphates (dNTPs) comprising 5-100 μM dGTP under suitable conditions for telomerase activity, optionally in the presence of an agent, thereby forming telomerase-extended DNA products; and (b) analyzing the telomerase-extended DNA products to determine the processivity of said telomerase.

In the telomerase primer-extension reaction, telomerase adds six nucleotides (i.e., GGTTAG) as a single repeat to the telomeric DNA primer. Thus, "telomerase processivity" is defined herein as the number of GGTTAG telomeric DNA repeats added to the DNA primer in a processive telomerase reaction.

The telomerase used with the present methods may be from any source and any species. Ideally, the telomerase is selected with the intended application in mind. For example, it may be advantageous to use a human telomerase for application in which the disclosed methods are used to identify drugs that affect telomerase processivity in human patients. In some embodiments, the telomerase comprises a recombinant telomerase protein produced in cell culture. For instance, the inventors expressed recombinant telomerase in human HEK293 cells, lysed the cells, and used the resulting cell lysate as a source of telomerase (see Examples). Methods for expressing recombinant protein and preparing cell extracts are well known in the art. Moreover, recombinant telomerase can be synthesized in vitro using lysates prepared from a variety of cell types, such as rabbit reticulocytes or human HELA cells. Many such in vitro protein expression systems are commercially available.

The methods and kits of the present invention may be used to assess telomerase processivity in any sample of interest. Suitable samples include, without limitation, a cell sample, tissue sample, or tumor sample. Telomerase is expressed by immortal human cells, including germline cells, embryonic cells, and certain types of tumor and cancer cells, but is not expressed by normal somatic cells. Thus, the methods of the present invention may be used to diagnose cells as cancerous based on high levels of telomerase processivity. Suitable samples for such purposes include samples obtained from various organs/tissues in a human patient as well as samples obtained from agriculturally important mammals (e.g., cattle, horses, pigs, and sheep) or any other animal of veterinary interest (e.g., cats and dogs).

As used herein, the term "telomeric DNA primer" refers to a DNA oligonucleotide that can be extended by telomerase in vitro (i.e., a telomerase substrate). The sequence of the native telomeric DNA repeat, GGTTAG, is conserved across all vertebrates and most metazoa, but it contains variations in other eukaryotes. Given that the telomerase expressed by one organism may differ from that of another organism with respect to substrate specificity, it may be advantageous to design the telomeric DNA primer in accordance with the origin of the telomerase. A suitable telomeric DNA primer may contain multiple telomeric repeats, a single telomeric repeat, or only part of a single telomeric repeat. In any case, the repeat(s) or portion thereof should be positioned at the 3'-end of the primer to facilitate base-pairing with the template sequence in the RNA component of the telomerase enzyme, ensuring that the DNA primer can be recognized and extended by the telomerase enzyme in the primer-extension reaction (see, e.g., FIG. 4).

Figure 8:
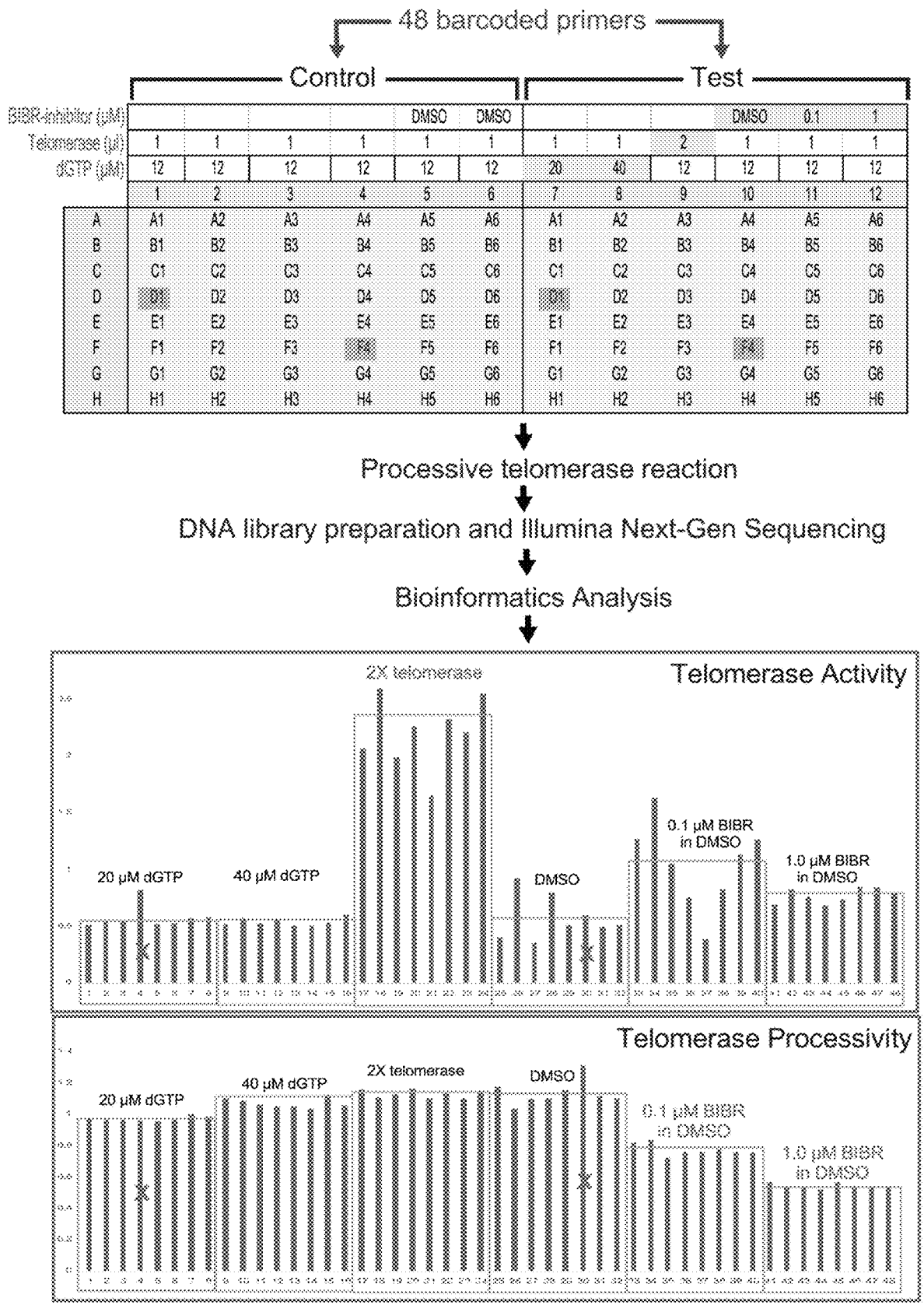
FIG. 8 shows the results of a high-throughput telomerase analysis. A total of 48 telomeric DNA primers, each comprising a randomized 7-nucleotide barcode sequence, were tested in this analysis. Each primer was used in several telomerase reactions under various conditions (i.e., various concentrations of the telomerase inhibitor BIBR, telomerase, and dGTP) and in mock reactions, as is outlined in the table at the top of the figure. The resulting extension products were pooled, used to prepare libraries for Illumina next-generation DNA sequencing, and the sequencing reads were analyzed. The graphs at the bottom of the figure show the levels of telomerase activity and telomerase processivity that were achieved using each of the 48 primers.

The methods of the present invention may be performed in a high-throughput format in which the telomerase-extended DNA products generated in many individual reactions are pooled and analyzed in a single sequencing reaction. To allow the products generated by each individual reaction (e.g., in the presence of specific agent) to be tracked, a telomeric DNA primer comprising a unique nucleotide barcode may be used in each individual reaction. As used herein, the term "nucleotide barcode" refers to an oligonucleotide tag sequence that allows a corresponding nucleic acid sequence to be identified (e.g., via computational data analysis). The present inventors discovered that constraining the nucleotide barcode within a stem loop structure (see, e.g., FIG. 3) prevents base-pairings between the barcode and neighboring sequences, which could interfere with primer function. Thus, in some embodiments, the nucleotide barcode is flanked by sequences that form a stem such that the nucleotide barcode resides within the loop region of a stem-loop structure in the primer. The inventors have discovered that certain barcode sequences can promote or inhibit telomerase activity (see, e.g., FIG. 8), which could bias the results of the present methods. Thus, in preferred embodiments, the selected nucleotide barcode sequences have a neutral effect on telomerase activity. Notably, the effect that each nucleotide barcode sequence has on telomerase activity must be determined experimentally, e.g., by comparing its effect to that of a neutral sequence in a telomerase primer-extension reaction. In Table 1, the inventors provide a list of 768 unique barcodes that do not interfere with telomerase function. Thus, in some embodiments, the nucleotide barcode sequence is selected from the sequences listed in Table 1.

Importantly, the inventors optimized several conditions of the telomerase primer-extension reaction performed in step (a) to ensure that the present methods are sensitive enough that changes in telomerase processivity (e.g., due to the presence of a telomerase inhibiting/enhancing agent) are readily apparent. In previous work, the inventors identified the incorporation of a specific dGTP nucleotide as the rate-limiting step in the human telomerase catalytic cycle (EMBO J. (2018) 37 (6): e97953), and have used this discovery to slow down and sensitize the telomerase primer-extension reaction in the present invention. Specifically, the concentration of dGTP is reduced from the conventional 1 mM to 5-100 μM in the reaction to limit the number of nucleotides added to the telomeric DNA primer. In addition to increasing the sensitivity of the assay, this also serves to reduce the cost of DNA sequencing analysis by allowing the added repeats to be covered by shorter sequencing reads. Notably, the concentration of the non-rate-limiting dNTPs in the reaction can be substantially higher. For example, in some embodiments, the dNTPs comprise 100-1000 μM dATP and 100-1000 μM dTTP. (Note: Telomerase does not utilize dCTP.) The higher concentrations of dATP and dTTP help to prevent premature termination of DNA repeat synthesis during each telomerase catalytic cycle, which generates products that are not compatible with the subsequent adapter-ligation step.

The sensitivity of this assay was further increased by reducing the reaction temperature from 37° C. to room temperature (25° C.), thereby reducing the reaction rate. Notably, this also simplifies the procedure by eliminating the need for a heating device (e.g., a thermocycler or an incubator). In conjunction, the length of the telomerase primer-extension reaction was adjusted to 20-30 minutes, which allows 4-5 repeat additions to occur at room temperature in the presence of 10-20 µM dGTP. Thus, in some embodiments of the disclosed methods, the incubating in step (a) is performed for 30 minutes at room temperature. Notably, the reaction may be terminated after a precise amount of time (e.g., after 30 minutes) by quenching the reaction (e.g., by adding EDTA). In preferred embodiments, the telomerase performs 4-5 repeat additions in step (a). Those of skill in the art will readily understand that the time and temperature are reaction conditions that may be altered within a reasonable range. For example, a similar reaction outcome may be achieved while varying the reaction temperature between 16-37° C. and varying the reaction time between 10 minutes and an hour. In general, the time should be reduced at higher temperatures, and vice versa, to achieve the same outcome.

The present methods may be used to identify agents that enhance or inhibit telomerase repeat addition processivity. As used herein, the term "agent" refers any substance that could potentially enhance or inhibit telomerase processivity. Suitable agents include therapeutic agents, such as pharmaceuticals, biologics, toxins, alkylating agents, enzymes, antibiotics, antimetabolites, antiproliferative agents, chemotherapeutic agents, hormones, neurotransmitters, DNA, RNA, siRNA, oligonucleotides, antisense RNA, aptamers, lectins, compounds that alter cell membrane permeability, photochemical compounds, small molecules, recombinant proteins or peptides, liposomes, micelles, gene therapy vectors, viral vectors, immunological therapeutic constructs, and other drugs. In some embodiments, the agent is a small molecule. In some embodiments, the agent is a potential anti-cancer drug or a potential anti-aging drug.

The analysis step (step b) may comprise any method by which telomerase processivity (i.e., the number of repeat additions added to the telomerase-extended DNA products) may be assessed. In some embodiments, processivity is assayed by running out telomerase-extended DNA products that have been labeled via incorporation of radioactive nucleotides in step (a) on a high-resolution polyacrylamide electrophoresis gel for visualization (see, e.g., FIG. 2B). Here, bands with lower mobility (i.e., those on the higher part of the gel in FIG. 2B) represent products with more repeats added, while the bands with higher mobility (i.e., those on the lower part of the gel in FIG. 2B) represent products with fewer repeats added. A telomerase primer-extension reaction with higher repeat addition processivity will generate more DNA products with more repeats added (i.e. higher intensity bands with lower mobility). In other embodiments, the analysis step comprises sequencing the telomerase-extended DNA products. Any sequencing method may be used with the present invention. Suitable methods include, for example, Sanger sequencing, Illumina sequencing, single molecule real time (SMRT) sequencing, Nanopore DNA sequencing, massively parallel signature sequencing (MPSS), Polony sequencing, 454 pyrosequencing, combinatorial probe anchor synthesis (cPAS), Ion Torrent semiconductor sequencing, DNA nanoball sequencing, and SOLID sequencing. For high-throughput applications, the sequencing method is advantageously a next-generation sequencing method.

In some embodiments, the method further comprises adding sequencing adapters to the ends of the telomerase-extended DNA products prior to step (b) to enable next-generation sequencing. As used herein, "sequencing adapters" are short DNA oligonucleotides that contain (1) sequences needed to amplify the DNA fragment during the sequencing reaction, and (2) sequences that interact with the sequencing platform (e.g., the surface of the Illumina flowcell or Ion Torrent beads). Accordingly, sequencing adapters should be selected based on the sequencing platform that is to be used. Sequencing adapters are commonly used to add "barcodes" to DNA sequences prior to high-throughput sequencing. Thus, in the present invention, using the sequencing adapters to incorporate a second indexing system allows a greater number of samples to be pooled in a single sequencing reaction. Many index sequences and adapter sets are commercially available and include, for example, Unique Dual Index (UDI) Adapters from IDT, TruSeq UD Indexes from Illumina, and SeqCap Dual End Adapters from Roche. In some embodiments, the sequencing adapters are added using polymerase chain reaction (PCR), e.g., using PCR primers that comprise the sequencing adapter sequences.

The methods of the present invention were designed to allow the telomerase-extended DNA products generated in many individual reactions to be pooled and analyzed in a single sequencing reaction. In some embodiments, the telomerase-extended DNA products are pooled from at least 300 reactions, from at least 3,000 reaction, or from at least 30,000 reactions, and are sequenced in the same sequencing reaction. Advantageously, the sequencing methods used in such embodiments should provide a sufficient number of reads per reaction such that the number of reads assigned to each individual telomerase primer-extension reaction will be enough to distinguish reactions with various levels of telomerase activity and processivity. For example, a single Illumina DNA sequencing reaction typically produces >300,000,000 reads. Thus, for a sequencing run containing DNA products from 30,000 reactions, about 10,000 reads should be assigned to each individual telomerase primer-extension reaction. This number of reads is expected to be more than sufficient to distinguish between reactions with different levels of telomerase activity and processivity.

The methods of the present invention are readily adapted to a high-throughput format. In such embodiments, the method is performed in a multi-well plate and a unique telomeric DNA primer is added to each well of the multi-well plate in step (a). Suitable multi-well plates include, for example, plates with 6, 12, 24, 48, 96, 384 or 1536 wells. To perform the present methods in a high-throughput format, it may be advantageous to employ a robotic liquid handling system (e.g., Beckman Coulter Biomek FX) to automate reaction setup in step (a).

Advantageously, residual telomeric DNA primers are removed from the telomerase-extended DNA products prior to the analysis step (i.e., to avoid wasting sequencing reads). However, the modest size difference between the telomeric DNA primer and the telomerase-extended DNA products makes it challenging to separate these oligonucleotides using traditional methods (e.g., size selection using magnetic beads or electrophoresis and gel extraction). Thus, in some embodiments, the methods further comprise ligating a hairpin adapter to the telomerase-extended DNA products produced in step (a) prior to step (b). The hairpin adapter used with the present invention comprises: (a) a sequence that is complementary to the 3' end of the telomerase-extended DNA products; (b) a 5' phosphate to allow for ligation with the telomerase-extended DNA products; (c) a purification moiety; and (d) PCR primer binding site.

Figure 4:
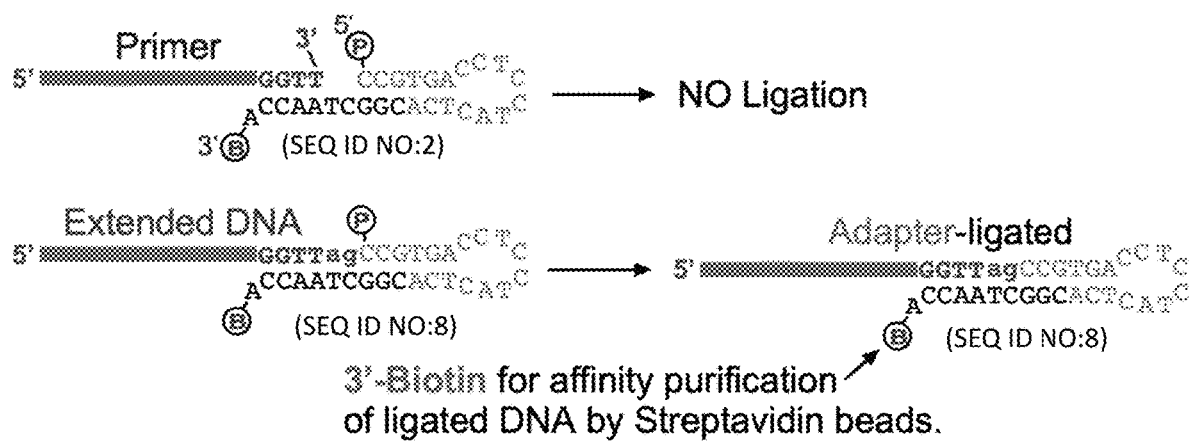
FIG. 4 is a schematic illustrating how the hairpin adapter is specifically ligated to the telomerase-extended DNA products but not to the un-extended primers.

To increase the specificity of the hairpin adaptor for the telomerase-extended DNA products, in some embodiments, the hairpin adapter further comprises (e) a stem-loop structure comprising a double-stranded stem and a single-stranded loop; and (f) a single-stranded 3'-overhang. This stem-loop structure reduces non-specific binding with residual primer by limiting the single-stranded regions of the hairpin adaptor to those that hybridize with the telomerase-extended DNA products (a) and the PCR primer (d). For example, in one specific embodiment, the hairpin adapter sequence forms a stem-loop comprising a 5-6 base-paired stem and an 8-10 nucleotide loop, which is followed by a single-stranded 3'-overhang comprising 6-7 nucleotides (FIG. 4). In some embodiments, the sequence that is complementary to the 3' end of the telomerase-extended DNA products is located within the single-stranded 3'-overhang. As used herein, the terms "complementary" refers to the ability of a nucleic acid molecule to bind to (i.e., hybridize with) another nucleic acid molecule through the formation of hydrogen bonds between specific nucleotides (i.e., A with T or U; G with C), forming a double-stranded molecule.

As used herein, the term "PCR primer binding site" refers to a sequence within the hairpin adaptor that is complementary to a PCR primer. Inclusion of this sequence, thus, facilitates binding of the PCR primer to the hairpin adapter-ligated telomerase-extended DNA products in a subsequent amplification step. In some embodiments, the PCR primer binding site is contained within the single-stranded loop of the hairpin adaptor (i.e., to ensure that it is accessible to the primer). In the present methods, PCR amplification may be used, for example, to convert the adapter-ligated DNA products into a double-stranded DNA amplicon library that is compatible with a next-generation sequencing platform of choice (e.g., Illumina). Notably, the PCR primers used to prepare a sequencing library should comprise appropriate sequencing adapter sequences to ensure that the resulting library is compatible with the sequencing platform of choice.

As used herein, a "purification moiety" refers to a tag or molecule that is appended to the hairpin adapter to facilitate purification of the hairpin adapter and any DNA ligated thereto. In some embodiments, the method further comprises affinity purifying the telomerase-extended DNA products using the purification moiety of the hairpin adaptor after the telomerase-extended DNA products are ligated to the hairpin adaptor. For instance, in the Examples, the inventors use a hairpin adapter that comprises a biotin tag derivative (i.e., biotin-triethyleneglycol) as a purification moiety and affinity purification is performed using streptavidin-coated beads. Other suitable purification moieties include, without limitation, chitin binding protein (CBP), hemagglutinin (HA), maltose binding protein (MBP), strep-tag, cMyc, poly(His) tag, Flag tag, V5 tag, NE-tag, glutathione-S-transferase (GST), and the like.

The 5' phosphate of the hairpin adaptor allows it to be ligated to the telomerase-extended DNA products using a standard DNA ligation reaction. For example, in some embodiments, the hairpin adaptor is ligated using a DNA ligase in a 1-hour ligation reaction performed at 30° C. Notably, the inventors have experimentally determined that the hairpin adapter should be used at a minimal concentration of 10 nM and should comprise a minimum of 6 nucleotides in the 3'-overhang complementary region to ensure adequate base-pairing to the telomerase-extended DNA products and efficient ligation. Thus, in some embodiments, the 3'-overhang in the hairpin adapter is at least 6 nucleotides in length, and in some embodiments, the concentration of the hairpin adaptor is at least 10 nM.

Kits:

The present invention also provides kits for performing the telomerase processivity assay disclosed herein. The kits comprise at least one telomeric DNA primer and dNTP mix comprising 5-100 µM dGTP, 100-1000 µM dTTP, and 100-100 µM dATP.

In some embodiments, the kits further comprise at least one of the following: purified telomerase, primer extension buffer, a barcoded telomeric DNA primer, a hairpin adapter, a PCR primer set, and a DNA ligase.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Examples

The following Example describes the development of an ultra-high-throughput screening assay for screening for small molecules that can effectively enhance the intrinsic activity of the telomerase enzyme and delay cellular aging in adult stem cells. Specifically, this assay is designed to assess the repeat addition processivity of telomerase enzymes in the stem cells.

Telomerase Primer-Extension Reaction

For this assay, telomerase was prepared from HEK293 cells that have been engineered to overexpress the two essential telomerase components of this enzyme, TERT and TR. A total of $3 \times 10^5$ telomerase-expressing HEK293 cells was lysed in 200 µl HEPES lysis buffer (20 mM HEPES-KOH, pH 7.9, 2 mM $MgCl_2$, 400 mM NaCl, 0.2 mM EGTA, 10% glycerol, 1 mM DTT, 1 mM PMSF and protease inhibitor) at 4° C. for 20 min, followed by centrifugation at 16,000×g at 4° C. for 15 min to remove cellular debris.

In a typical telomerase primer-extension reaction, telomerase adds six nucleotides (i.e., GGTTAG) as a single repeat to the primer. Telomerase is processive, meaning that it is capable of adding multiple DNA repeats in a single turnover reaction (FIG. 2A).

The telomerase primer-extension reaction can be performed for 30 min at room temperature. Each 10 µl reaction may comprise 2 µl of HEK293 cell lysate, 0.1 µM telomeric DNA primer, 12 µM dGTP, 300 µM dATP, 300 µM dTTP, and 1× primer extension buffer. (Note: telomerase does not utilize dCTP.) This reaction may be terminated (e.g., after precisely 30 min) by the addition of 10 mM EDTA. Reaction setup may be performed using a robotic liquid handling system (e.g., Beckman Coulter BIOMEK FX automated workstation).

Figure 2B:
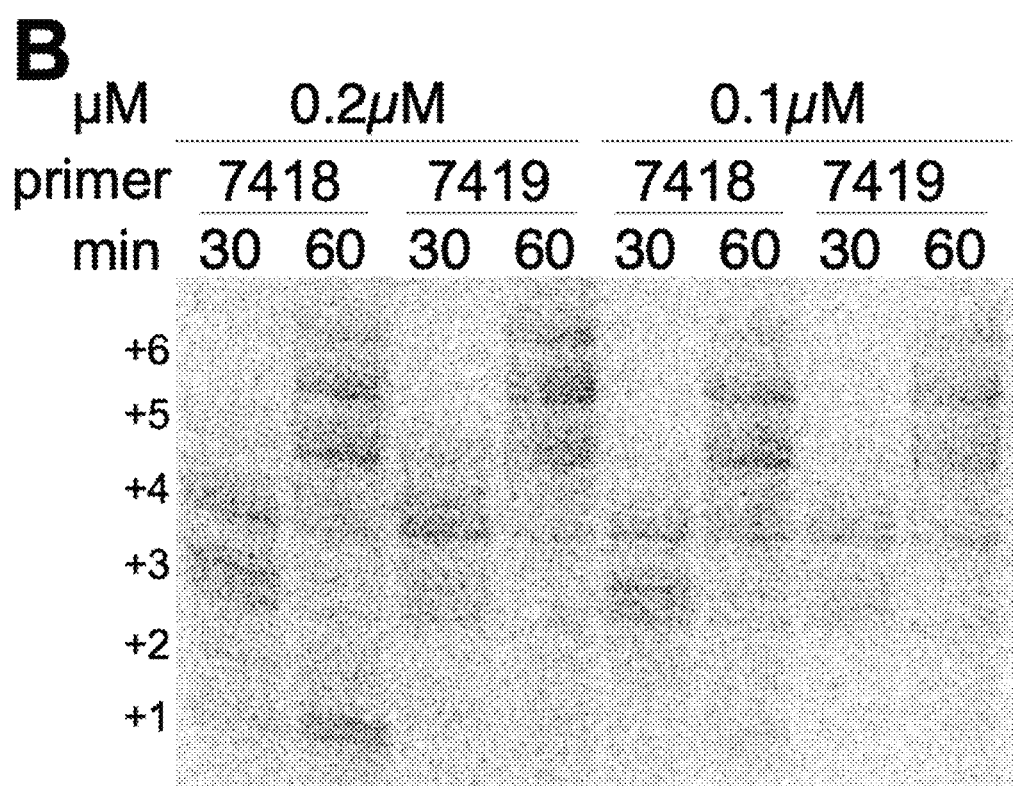
FIG. 2B shows the optimization of telomerase primer-extension reaction conditions. Telomerase repeat addition activity was assessed in the presence of two primers ("ASU-7418" (SEQ ID NO: 9) and "ASU-7419" (SEQ ID NO:10)) tested at two concentrations (0.1 µM and 0.2 µM) in a reaction performed at room temperature for either 30 or 60 min.

Importantly, several conditions of this reaction were optimized to ensure that the assay was both sensitive and cost effective. Telomerase activity and processivity are highly sensitive to the concentration of dGTP and vary dramatically within the range of 5 to 100 µM dGTP. Thus, in this assay, the telomerase primer-extension reaction is performed in the presence of 12 µM dGTP to minimize the number of nucleotides added to the primer. This serves to (1) reduce the cost of DNA sequencing analysis by allowing the added repeats to be covered by shorter sequencing reads, and (2) increase the sensitivity of the assay by slowing down telomerase enough to detect changes in its activity in the presence of enhancers or inhibitors. The sensitivity of the assay was further increased by reducing the reaction temperature from 37° C. to room temperature (25° C.), which both reduces the reaction rate and simplifies the procedure (i.e., by eliminating the need for a heating device). In conjunction, the length of the reaction was adjusted to 30 min, allowing 4-5 repeat additions to occur at room temperature. The cost per reaction is further reduced by designing the assay to use a minimal concentration of the DNA primer (FIG. 2B).

Barcoded Telomerase DNA Primers

Figure 3:
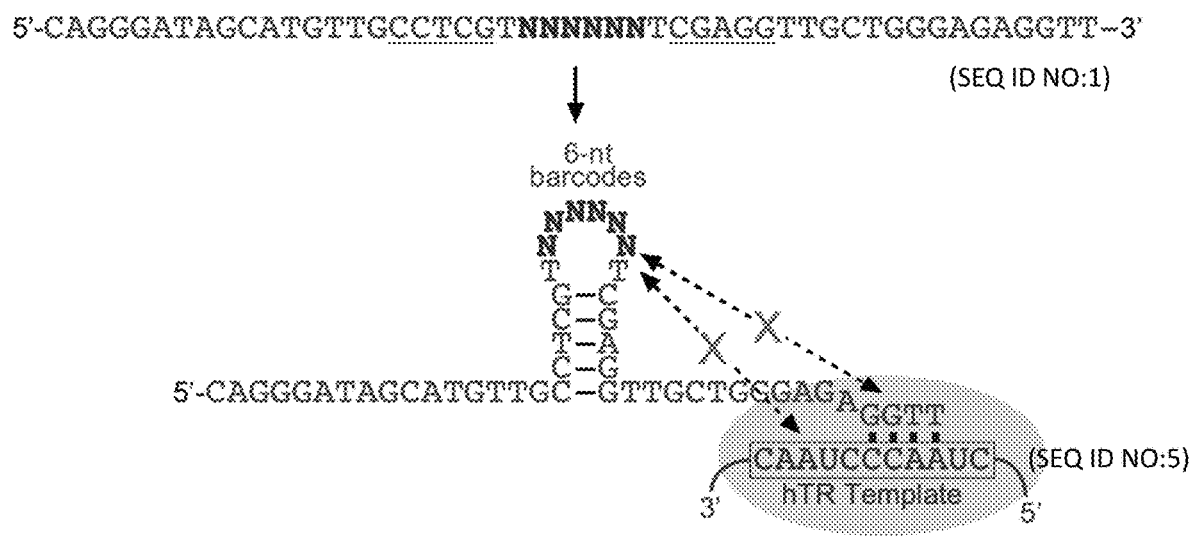
FIG. 3 is a schematic depicting the secondary structure of a barcoded telomerase DNA primer. The barcode sequence is constrained within a stem loop to prevent it from interacting with neighboring sequences in the primer or the TR template sequence, which could affect telomerase activity.

The extended DNA products synthesized by telomerase in each well of the 384-well plate may be pooled and processed together in a single tube to generate a DNA library for Illumina sequencing. To track the DNA products produced in each individual well in the presence of a specific small molecule, each reaction mixture may contain a unique telomeric DNA primer that has been modified to include a structurally defined 6-nucleotide barcode (e.g., 5'-CAGG-GATAG-CATGTTGCCTCGTNNNNNNTCGAGGTTGCTGG-GAGAGGTT-3' (SEQ ID NO: 1), wherein the barcode is represented by the NNNNNN). These primers have been designed such that the barcode sequences are flanked by two sequences (underlined) that form a 5-bp stem, which constrains the barcode sequence to a stem loop (FIG. 3). This design is intended to prevent base-pairings between the barcode and the neighboring sequence (especially the 3'-end of the primer, which is crucial for telomerase primer-extension activity) from interfering with primer function.

Moreover, to avoid biasing the results of a screen, the specific barcode sequences used in the assay must be experimentally tested to ensure that their effect on telomerase activity is neutral. The ability of barcode sequences to promote or inhibit telomerase activity was tested in FIG. 8. A total of 48 primers, each comprising a randomized 7-nucleotide barcode sequence, were used in this experiment. The results of this experiment demonstrate that certain barcode sequences can promote or inhibit telomerase activity.

A total of 768 unique telomeric DNA primers have been designed, each comprising a different barcode sequence that does not interfere with telomerase function. The barcode sequences used in these primers and are provided in Table 1, below. Use of these primers allows 384 telomerase primer-extension reactions to performed in duplicate simultaneously. Each barcode will be assigned to a specific reaction in which a particular compound is tested for its ability to impact telomerase activity. Thus, this assay will produce up to 384 uniquely barcoded DNA products from each 384-well plate, which will be pooled and purified together in a single tube using the Oligo Clean & Concentrator™ (Zymo Research) and eluted in 10-20 µl $H_2O$.

TABLE 1

| Barcode sequences used in the 786 telomeric DNA primers | |
|---|---|
| 1 | ACCCTTG |
| 2 | CCCCTTG |
| 3 | CCCTTTT |
| 4 | CCGCTTG |
| 5 | CCGCTTT |
| 6 | CCGGCTT |
| 7 | CCGGTTG |
| 8 | CCGGTTT |
| 9 | CCGTCTT |

TABLE 1-continued

Barcode sequences used in the 786 telomeric DNA primers

| # | Sequence |
|---|---|
| 10 | CCGTTGT |
| 11 | CCGTTTT |
| 12 | CCTCCGT |
| 13 | CCTCCTT |
| 14 | CCTCGGT |
| 15 | CCTCGTG |
| 16 | CCTCTGT |
| 17 | CCTCTTG |
| 18 | CCTGCTT |
| 19 | CCTGTGT |
| 20 | CCTGTTG |
| 21 | CCTGTTT |
| 22 | CCTTCTG |
| 23 | CCTTGGT |
| 24 | CCTTGTG |
| 25 | CCTTTCG |
| 26 | CCTTTCT |
| 27 | CCTTTGG |
| 28 | CCTTTGT |
| 29 | CCTTTTG |
| 30 | CCTTTTT |
| 31 | CGCCCTT |
| 32 | CGCCGTT |
| 33 | CGCCTTG |
| 34 | CGCGCTT |
| 35 | CGCGGTT |
| 36 | CGCGTTG |
| 37 | CGCGTTT |
| 38 | CGCTCGT |
| 39 | CGCTCTT |
| 40 | CGCTTCT |
| 41 | CGCTTGT |
| 42 | CGCTTTG |
| 43 | CGCTTTT |
| 44 | CGGCCTT |
| 45 | CGGCGTT |
| 46 | CGGCTTT |
| 47 | CGGGCTT |
| 48 | CGGGTCT |
| 49 | CGGGTTG |
| 50 | CGGGTTT |
| 51 | CGGTCGT |
| 52 | CGGTCTG |
| 53 | CGGTCTT |
| 54 | CGGTGTG |
| 55 | CGGTGTT |
| 56 | CGGTTCG |
| 57 | CGGTTCT |
| 58 | CGGTTGT |
| 59 | CGGTTTT |
| 60 | CGTCCGT |
| 61 | CGTCCTT |
| 62 | CGTCGCT |
| 63 | CGTCGGT |
| 64 | CGTCGTG |
| 65 | CGTCGTT |
| 66 | CGTCTCG |
| 67 | CGTCTTT |
| 68 | CGTGCGT |
| 69 | CGTGCTT |
| 70 | CGTGGGT |
| 71 | CGTGGTG |
| 72 | CGTGTCT |
| 73 | CGTGTGG |
| 74 | CGTGTGT |
| 75 | CGTGTTG |
| 76 | CGTGTTT |
| 77 | CGTTCCT |
| 78 | CGTTCGT |
| 79 | CGTTCTG |
| 80 | CGTTCTT |
| 81 | CGTTGCG |
| 82 | CGTTGGG |
| 83 | CGTTGGT |
| 84 | CGTTGTG |
| 85 | CGTTGTT |

TABLE 1-continued

Barcode sequences used in the 786 telomeric DNA primers

| | |
|---|---|
| 86 | CGTTTCG |
| 87 | CGTTTCT |
| 88 | CGTTTGC |
| 89 | CGTTTGG |
| 90 | CGTTTGT |
| 91 | CGTTTTC |
| 92 | CGTTTTG |
| 93 | CGTTTTT |
| 94 | CTCCCTT |
| 95 | CTCCGCT |
| 96 | CTCCGGT |
| 97 | CTCCGTG |
| 98 | CTCCGTT |
| 99 | CTCCTCG |
| 100 | CTCCTTG |
| 101 | CTCCTTT |
| 102 | CTCGCGT |
| 103 | CTCGCTG |
| 104 | CTCGCTT |
| 105 | CTCGGGT |
| 106 | CTCGTCT |
| 107 | CTCGTGG |
| 108 | CTCGTGT |
| 109 | CTCGTTG |
| 110 | CTCGTTT |
| 111 | CTCTCGG |
| 112 | CTCTCGT |
| 113 | CTCTCTG |
| 114 | CTCTCTT |
| 115 | CTCTTCG |
| 116 | CTCTTCT |
| 117 | CTCTTGG |
| 118 | CTCTTGT |
| 119 | CTCTTTG |
| 120 | CTCTTTT |
| 121 | CTGCCGT |
| 122 | CTGCGGT |
| 123 | CTGCGTG |
| 124 | CTGCGTT |
| 125 | CTGCTCT |
| 126 | CTGCTTG |
| 127 | CTGCTTT |
| 128 | CTGGCGT |
| 129 | CTGGGTG |
| 130 | CTGGGTT |
| 131 | CTGGTCT |
| 132 | CTGGTGT |
| 133 | CTGGTTG |
| 134 | CTGGTTT |
| 135 | CTGTCCG |
| 136 | CTGTCCT |
| 137 | CTGTCGG |
| 138 | CTGTCTG |
| 139 | CTGTCTT |
| 140 | CTGTGCT |
| 141 | CTGTGGT |
| 142 | CTGTGTT |
| 143 | CTGTTCG |
| 144 | CTGTTGG |
| 145 | CTGTTGT |
| 146 | CTGTTTC |
| 147 | CTGTTTG |
| 148 | CTTCCCT |
| 149 | CTTCCGT |
| 150 | CTTCCTT |
| 151 | CTTCGCG |
| 152 | CTTCGGG |
| 153 | CTTCGGT |
| 154 | CTTCGTG |
| 155 | CTTCGTT |
| 156 | CTTCTCG |
| 157 | CTTCTGG |
| 158 | CTTCTGT |
| 159 | CTTCTTC |
| 160 | CTTCTTG |
| 161 | CTTCTTT |

TABLE 1-continued

Barcode sequences used in the 786 telomeric DNA primers

| | |
|---|---|
| 162 | CTTGCCT |
| 163 | CTTGCTG |
| 164 | CTTGCTT |
| 165 | CTTGGCT |
| 166 | CTTGGGT |
| 167 | CTTGGTT |
| 168 | CTTGTCG |
| 169 | CTTGTCT |
| 170 | CTTGTGG |
| 171 | CTTGTGT |
| 172 | CTTGTTG |
| 173 | CTTGTTT |
| 174 | CTTTCCG |
| 175 | CTTTCGG |
| 176 | CTTTCGT |
| 177 | CTTTCTC |
| 178 | CTTTCTG |
| 179 | CTTTCTT |
| 180 | CTTTGCG |
| 181 | CTTTGCT |
| 182 | CTTTGGT |
| 183 | CTTTGTG |
| 184 | CTTTGTT |
| 185 | CTTTTCG |
| 186 | CTTTTGC |
| 187 | CTTTTGG |
| 188 | CTTTTGT |
| 189 | CTTTTTG |
| 190 | CTTTTTT |
| 191 | GCCCGTT |
| 192 | GCCCTGT |
| 193 | GCCCTTT |
| 194 | GCCGCTT |
| 195 | GCCGTTT |
| 196 | GCCTCTT |
| 197 | GCCTGTT |
| 198 | GCCTTGG |
| 199 | GCCTTGT |
| 200 | GCCTTTG |
| 201 | GCCTTTT |
| 202 | GCGCCTT |
| 203 | GCGCGTT |
| 204 | GCGCTCT |
| 205 | GCGCTTG |
| 206 | GCGCTTT |
| 207 | GCGGCTT |
| 208 | GCGGGTT |
| 209 | GCGGTGT |
| 210 | GCGGTTT |
| 211 | GCGTCTG |
| 212 | GCGTCTT |
| 213 | GCGTGGT |
| 214 | GCGTGTT |
| 215 | GCGTTCG |
| 216 | GCGTTGT |
| 217 | GCGTTTC |
| 218 | GCGTTTG |
| 219 | GCGTTTT |
| 220 | GCTCCGT |
| 221 | GCTCCTT |
| 222 | GCTCGCT |
| 223 | GCTCGGT |
| 224 | GCTCGTC |
| 225 | GCTCGTG |
| 226 | GCTCGTT |
| 227 | GCTCTCG |
| 228 | GCTCTCT |
| 229 | GCTCTGG |
| 230 | GCTCTGT |
| 231 | GCTCTTC |
| 232 | GCTCTTG |
| 233 | GCTCTTT |
| 234 | GCTGCTG |
| 235 | GCTGCTT |
| 236 | GCTGGGT |
| 237 | GCTGGTT |

TABLE 1-continued

Barcode sequences used in the 786 telomeric DNA primers

| | |
|---|---|
| 238 | GCTGTGT |
| 239 | GCTGTTT |
| 240 | GCTTCCG |
| 241 | GCTTCCT |
| 242 | GCTTCTT |
| 243 | GCTTGCT |
| 244 | GCTTGGT |
| 245 | GCTTGTC |
| 246 | GCTTGTG |
| 247 | GCTTGTT |
| 248 | GCTTTCG |
| 249 | GCTTTGC |
| 250 | GCTTTGT |
| 251 | GCTTTTC |
| 252 | GCTTTTG |
| 253 | GCTTTTT |
| 254 | GGCCCTT |
| 255 | GGCCGTT |
| 256 | GGCCTTT |
| 257 | GGCGCTT |
| 258 | GGCGGTT |
| 259 | GGCGTTT |
| 260 | GGCTCGT |
| 261 | GGCTCTC |
| 262 | GGCTCTT |
| 263 | GGCTGGT |
| 264 | GGCTGTT |
| 265 | GGCTTCG |
| 266 | GGCTTCT |
| 267 | GGCTTGC |
| 268 | GGCTTGG |
| 269 | GGCTTGT |
| 270 | GGCTTTC |
| 271 | GGCTTTG |
| 272 | GGGCTTT |
| 273 | GGGGTCT |
| 274 | GGGGTTG |
| 275 | GGGGTTT |
| 276 | GGGTCTT |
| 277 | GGGTGTT |
| 278 | GGGTTGT |
| 279 | GGGTTTT |
| 280 | GGTCCCT |
| 281 | GGTCCGT |
| 282 | GGTCCTC |
| 283 | GGTCCTG |
| 284 | GGTCCTT |
| 285 | GGTCGCT |
| 286 | GGTCGTC |
| 287 | GGTCGTT |
| 288 | GGTCTCC |
| 289 | GGTCTCT |
| 290 | GGTCTGT |
| 291 | GGTCTTC |
| 292 | GGTCTTG |
| 293 | GGTCTTT |
| 294 | GGTGCGT |
| 295 | GGTGCTC |
| 296 | GGTGCTT |
| 297 | GGTGGCT |
| 298 | GGTGTCT |
| 299 | GGTGTGT |
| 300 | GGTGTTG |
| 301 | GGTGTTT |
| 302 | GGTTCCG |
| 303 | GGTTCCT |
| 304 | GGTTCGC |
| 305 | GGTTCGG |
| 306 | GGTTCTC |
| 307 | GGTTCTG |
| 308 | GGTTGCT |
| 309 | GGTTGGG |
| 310 | GGTTGTC |
| 311 | GGTTGTG |
| 312 | GGTTGTT |
| 313 | GGTTTCC |

TABLE 1-continued

Barcode sequences used in the 786 telomeric DNA primers

| | |
|---|---|
| 314 | GGTTTCG |
| 315 | GGTTTCT |
| 316 | GGTTTGG |
| 317 | GGTTTGT |
| 318 | GGTTTTC |
| 319 | GGTTTTG |
| 320 | GGTTTTT |
| 321 | GTCCCCT |
| 322 | GTCCCGT |
| 323 | GTCCCTT |
| 324 | GTCCGGT |
| 325 | GTCCGTG |
| 326 | GTCCGTT |
| 327 | GTCCTCG |
| 328 | GTCCTCT |
| 329 | GTCCTGT |
| 330 | GTCCTTC |
| 331 | GTCCTTG |
| 332 | GTCCTTT |
| 333 | GTCGCGT |
| 334 | GTCGCTG |
| 335 | GTCGCTT |
| 336 | GTCGGCT |
| 337 | GTCGGTG |
| 338 | GTCGGTT |
| 339 | GTCGTCT |
| 340 | GTCGTGT |
| 341 | GTCGTTG |
| 342 | GTCGTTT |
| 343 | GTCTCCG |
| 344 | GTCTCCT |
| 345 | GTCTCGC |
| 346 | GTCTCGG |
| 347 | GTCTCGT |
| 348 | GTCTCTC |
| 349 | GTCTCTG |
| 350 | GTCTCTT |
| 351 | GTCTGCT |

TABLE 1-continued

Barcode sequences used in the 786 telomeric DNA primers

| | |
|---|---|
| 352 | GTCTGGT |
| 353 | GTCTGTT |
| 354 | GTCTTGC |
| 355 | GTCTTGT |
| 356 | GTCTTTC |
| 357 | GTCTTTG |
| 358 | GTCTTTT |
| 359 | GTGCCCT |
| 360 | GTGCCTT |
| 361 | GTGCGCT |
| 362 | GTGCGGT |
| 363 | GTGCGTT |
| 364 | GTGCTCG |
| 365 | GTGCTCT |
| 366 | GTGCTGT |
| 367 | GTGCTTC |
| 368 | GTGCTTG |
| 369 | GTGGGTC |
| 370 | GTGGTCG |
| 371 | GTGGTCT |
| 372 | GTGGTTC |
| 373 | GTGGTTG |
| 374 | GTGTCCG |
| 375 | GTGTCCT |
| 376 | GTGTCGG |
| 377 | GTGTCGT |
| 378 | GTGTCTC |
| 379 | GTGTCTG |
| 380 | GTGTCTT |
| 381 | GTGTGCT |
| 382 | GTGTGGT |
| 383 | GTGTGTC |
| 384 | GTGTGTT |
| 385 | GTGTTCG |
| 386 | GTGTTCT |
| 387 | GTGTTGC |
| 388 | GTGTTGT |
| 389 | GTGTTTG |

TABLE 1-continued

Barcode sequences used in the 786 telomeric DNA primers

| | |
|---|---|
| 390 | GTGTTTT |
| 391 | GTTCCCT |
| 392 | GTTCCGG |
| 393 | GTTCCTC |
| 394 | GTTCCTG |
| 395 | GTTCGCG |
| 396 | GTTCGCT |
| 397 | GTTCGGT |
| 398 | GTTCGTC |
| 399 | GTTCGTG |
| 400 | GTTCGTT |
| 401 | GTTCTCT |
| 402 | GTTCTGC |
| 403 | GTTCTGT |
| 404 | GTTCTTC |
| 405 | GTTCTTG |
| 406 | GTTCTTT |
| 407 | GTTGCGG |
| 408 | GTTGCGT |
| 409 | GTTGCTC |
| 410 | GTTGCTG |
| 411 | GTTGGTC |
| 412 | GTTGGTG |
| 413 | GTTGGTT |
| 414 | GTTGTCG |
| 415 | GTTGTCT |
| 416 | GTTGTGC |
| 417 | GTTGTGG |
| 418 | GTTGTGT |
| 419 | GTTGTTC |
| 420 | GTTGTTG |
| 421 | GTTGTTT |
| 422 | GTTTCCG |
| 423 | GTTTCGT |
| 424 | GTTTCTC |
| 425 | GTTTCTG |
| 426 | GTTTCTT |
| 427 | GTTTGCG |
| 428 | GTTTGCT |
| 429 | GTTTGGC |
| 430 | GTTTGGG |
| 431 | GTTTGGT |
| 432 | GTTTGTC |
| 433 | GTTTGTG |
| 434 | GTTTTCC |
| 435 | GTTTTCG |
| 436 | GTTTTGC |
| 437 | GTTTTGG |
| 438 | GTTTTGT |
| 439 | GTTTTTG |
| 440 | GTTTTTT |
| 441 | TCCCCGG |
| 442 | TCCCCGT |
| 443 | TCCCCTG |
| 444 | TCCCCTT |
| 445 | TCCCGTT |
| 446 | TCCCTTG |
| 447 | TCCCTTT |
| 448 | TCCGCGT |
| 449 | TCCGCTG |
| 450 | TCCGGTG |
| 451 | TCCGGTT |
| 452 | TCCGTCT |
| 453 | TCCGTGT |
| 454 | TCCGTTG |
| 455 | TCCTCGG |
| 456 | TCCTCGT |
| 457 | TCCTCTT |
| 458 | TCCTGTT |
| 459 | TCCTTGG |
| 460 | TCCTTGT |
| 461 | TCCTTTG |
| 462 | TCCTTTT |
| 463 | TCGCCCT |
| 464 | TCGCCTT |
| 465 | TCGCGCT |

TABLE 1-continued

Barcode sequences used in the 786 telomeric DNA primers

| | |
|---|---|
| 466 | TCGCGGT |
| 467 | TCGCGTG |
| 468 | TCGCGTT |
| 469 | TCGCTCG |
| 470 | TCGCTCT |
| 471 | TCGCTTG |
| 472 | TCGCTTT |
| 473 | TCGGCGT |
| 474 | TCGGCTT |
| 475 | TCGGTCT |
| 476 | TCGGTTC |
| 477 | TCGGTTG |
| 478 | TCGGTTT |
| 479 | TCGTCCG |
| 480 | TCGTCGT |
| 481 | TCGTCTG |
| 482 | TCGTCTT |
| 483 | TCGTGGG |
| 484 | TCGTGGT |
| 485 | TCGTGTG |
| 486 | TCGTGTT |
| 487 | TCGTTCG |
| 488 | TCGTTGG |
| 489 | TCGTTGT |
| 490 | TCGTTTG |
| 491 | TCGTTTT |
| 492 | TCTCCCG |
| 493 | TCTCCGG |
| 494 | TCTCCGT |
| 495 | TCTCCTG |
| 496 | TCTCCTT |
| 497 | TCTCGCT |
| 498 | TCTCGGT |
| 499 | TCTCGTC |
| 500 | TCTCGTG |
| 501 | TCTCGTT |
| 502 | TCTCTCT |
| 503 | TCTCTGG |
| 504 | TCTCTGT |
| 505 | TCTCTTG |
| 506 | TCTCTTT |
| 507 | TCTGCCT |
| 508 | TCTGCGT |
| 509 | TCTGCTG |
| 510 | TCTGCTT |
| 511 | TCTGGTG |
| 512 | TCTGGTT |
| 513 | TCTGTCT |
| 514 | TCTGTGG |
| 515 | TCTGTGT |
| 516 | TCTGTTG |
| 517 | TCTGTTT |
| 518 | TCTTCGG |
| 519 | TCTTCTG |
| 520 | TCTTCTT |
| 521 | TCTTGCG |
| 522 | TCTTGCT |
| 523 | TCTTGGG |
| 524 | TCTTGGT |
| 525 | TCTTGTT |
| 526 | TCTTTCG |
| 527 | TCTTTGG |
| 528 | TCTTTGT |
| 529 | TCTTTTG |
| 530 | TGCCCCT |
| 531 | TGCCCGT |
| 532 | TGCCCTT |
| 533 | TGCCGCT |
| 534 | TGCCGTG |
| 535 | TGCCTGT |
| 536 | TGCGCGT |
| 537 | TGCGCTG |
| 538 | TGCGCTT |
| 539 | TGCGGGT |
| 540 | TGCGGTT |
| 541 | TGCGTCT |

TABLE 1-continued

Barcode sequences used in the 786 telomeric DNA primers

| # | Sequence |
|---|---|
| 542 | TGCGTGG |
| 543 | TGCGTGT |
| 544 | TGCGTTG |
| 545 | TGCGTTT |
| 546 | TGCTCCG |
| 547 | TGCTCGC |
| 548 | TGCTCGG |
| 549 | TGCTCGT |
| 550 | TGCTCTG |
| 551 | TGCTCTT |
| 552 | TGCTGCT |
| 553 | TGCTGGT |
| 554 | TGCTGTG |
| 555 | TGCTGTT |
| 556 | TGCTTCG |
| 557 | TGCTTGC |
| 558 | TGCTTGG |
| 559 | TGCTTTC |
| 560 | TGGCCTT |
| 561 | TGGCGCT |
| 562 | TGGCGGT |
| 563 | TGGCGTT |
| 564 | TGGCTCG |
| 565 | TGGCTTC |
| 566 | TGGCTTG |
| 567 | TGGCTTT |
| 568 | TGGGCCT |
| 569 | TGGGCTG |
| 570 | TGGGCTT |
| 571 | TGGGGCT |
| 572 | TGGGGTT |
| 573 | TGGGTCT |
| 574 | TGGGTGT |
| 575 | TGGGTTC |
| 576 | TGGGTTG |
| 577 | TGGGTTT |
| 578 | TGGTCCG |
| 579 | TGGTCGT |
| 580 | TGGTCTG |
| 581 | TGGTCTT |
| 582 | TGGTGCT |
| 583 | TGGTGGT |
| 584 | TGGTGTG |
| 585 | TGGTTCG |
| 586 | TGGTTCT |
| 587 | TGGTTGG |
| 588 | TGGTTGT |
| 589 | TGGTTTC |
| 590 | TGGTTTT |
| 591 | TGTCCCG |
| 592 | TGTCCCT |
| 593 | TGTCCGG |
| 594 | TGTCCTG |
| 595 | TGTCCTT |
| 596 | TGTCGCG |
| 597 | TGTCGCT |
| 598 | TGTCGGT |
| 599 | TGTCGTT |
| 600 | TGTCTCG |
| 601 | TGTCTGG |
| 602 | TGTCTGT |
| 603 | TGTCTTG |
| 604 | TGTCTTT |
| 605 | TGTGCCT |
| 606 | TGTGCGG |
| 607 | TGTGCGT |
| 608 | TGTGCTC |
| 609 | TGTGCTG |
| 610 | TGTGCTT |
| 611 | TGTGGTG |
| 612 | TGTGGTT |
| 613 | TGTGTGC |
| 614 | TGTGTGG |
| 615 | TGTGTGT |
| 616 | TGTGTTC |
| 617 | TGTGTTG |

TABLE 1-continued

Barcode sequences used in the 786 telomeric DNA primers

| | |
|---|---|
| 618 | TGTTCCG |
| 619 | TGTTCCT |
| 620 | TGTTCGC |
| 621 | TGTTCGT |
| 622 | TGTTCTG |
| 623 | TGTTCTT |
| 624 | TGTTGCG |
| 625 | TGTTGGG |
| 626 | TGTTGGT |
| 627 | TGTTGTC |
| 628 | TGTTGTG |
| 629 | TGTTTCG |
| 630 | TGTTTGG |
| 631 | TGTTTGT |
| 632 | TGTTTTG |
| 633 | TTCCCCG |
| 634 | TTCCCGT |
| 635 | TTCCCTG |
| 636 | TTCCCTT |
| 637 | TTCCGCG |
| 638 | TTCCGGG |
| 639 | TTCCGGT |
| 640 | TTCCGTG |
| 641 | TTCCTCG |
| 642 | TTCCTGT |
| 643 | TTCCTTG |
| 644 | TTCCTTT |
| 645 | TTCGCCG |
| 646 | TTCGCCT |
| 647 | TTCGCTC |
| 648 | TTCGCTG |
| 649 | TTCGCTT |
| 650 | TTCGGCT |
| 651 | TTCGGTG |
| 652 | TTCGGTT |
| 653 | TTCGTCG |
| 654 | TTCGTCT |
| 655 | TTCGTGG |
| 656 | TTCGTGT |
| 657 | TTCGTTC |
| 658 | TTCGTTG |
| 659 | TTCGTTT |
| 660 | TTCTCCG |
| 661 | TTCTCCT |
| 662 | TTCTCGG |
| 663 | TTCTCGT |
| 664 | TTCTCTC |
| 665 | TTCTCTG |
| 666 | TTCTCTT |
| 667 | TTCTGCT |
| 668 | TTCTGGG |
| 669 | TTCTGGT |
| 670 | TTCTGTG |
| 671 | TTCTTGC |
| 672 | TTCTTGG |
| 673 | TTCTTTG |
| 674 | TTCTTTT |
| 675 | TTGCCCG |
| 676 | TTGCCGT |
| 677 | TTGCCTG |
| 678 | TTGCCTT |
| 679 | TTGCGCG |
| 680 | TTGCGCT |
| 681 | TTGCGGG |
| 682 | TTGCGGT |
| 683 | TTGCGTG |
| 684 | TTGCTCT |
| 685 | TTGCTGT |
| 686 | TTGCTTC |
| 687 | TTGCTTG |
| 688 | TTGCTTT |
| 689 | TTGGCCG |
| 690 | TTGGCCT |
| 691 | TTGGCGT |
| 692 | TTGGCTT |
| 693 | TTGGGCT |

TABLE 1-continued

Barcode sequences used in the 786 telomeric DNA primers

| | |
|---|---|
| 694 | TTGGGTT |
| 695 | TTGGTGG |
| 696 | TTGGTGT |
| 697 | TTGGTTC |
| 698 | TTGGTTG |
| 699 | TTGGTTT |
| 700 | TTGTCCG |
| 701 | TTGTCCT |
| 702 | TTGTCGT |
| 703 | TTGTCTC |
| 704 | TTGTCTG |
| 705 | TTGTCTT |
| 706 | TTGTGCG |
| 707 | TTGTGCT |
| 708 | TTGTGGG |
| 709 | TTGTGGT |
| 710 | TTGTGTC |
| 711 | TTGTGTG |
| 712 | TTGTGTT |
| 713 | TTGTTCG |
| 714 | TTGTTGC |
| 715 | TTGTTGT |
| 716 | TTGTTTT |
| 717 | TTTCCCG |
| 718 | TTTCCCT |
| 719 | TTTCCGC |
| 720 | TTTCCGG |
| 721 | TTTCCTG |
| 722 | TTTCCTT |
| 723 | TTTCGCG |
| 724 | TTTCGCT |
| 725 | TTTCGGC |
| 726 | TTTCGGG |
| 727 | TTTCGGT |
| 728 | TTTCGTC |
| 729 | TTTCGTT |
| 730 | TTTCTCT |
| 731 | TTTCTGC |

TABLE 1-continued

Barcode sequences used in the 786 telomeric DNA primers

| | |
|---|---|
| 732 | TTTCTGG |
| 733 | TTTCTTG |
| 734 | TTTGCCG |
| 735 | TTTGCCT |
| 736 | TTTGCGC |
| 737 | TTTGCGG |
| 738 | TTTGCGT |
| 739 | TTTGCTC |
| 740 | TTTGCTG |
| 741 | TTTGCTT |
| 742 | TTTGGCG |
| 743 | TTTGGGT |
| 744 | TTTGGTG |
| 745 | TTTGGTT |
| 746 | TTTGTCG |
| 747 | TTTGTCT |
| 748 | TTTGTGG |
| 749 | TTTGTGT |
| 750 | TTTGTTG |
| 751 | TTTTCCG |
| 752 | TTTTCCT |
| 753 | TTTTCGC |
| 754 | TTTTCGG |
| 755 | TTTTCGT |
| 756 | TTTTCTG |
| 757 | TTTTCTT |
| 758 | TTTTGCG |
| 759 | TTTTGCT |
| 760 | TTTTGGC |
| 761 | TTTTGGG |
| 762 | TTTTGGT |
| 763 | TTTTGTG |
| 764 | TTTTTCG |
| 765 | TTTTTGC |
| 766 | TTTTTGG |
| 767 | TTTTTGT |
| 768 | TTTTTTG |

Ligation of Hairpin-Adapter to Extended DNA Products

Figure 5:
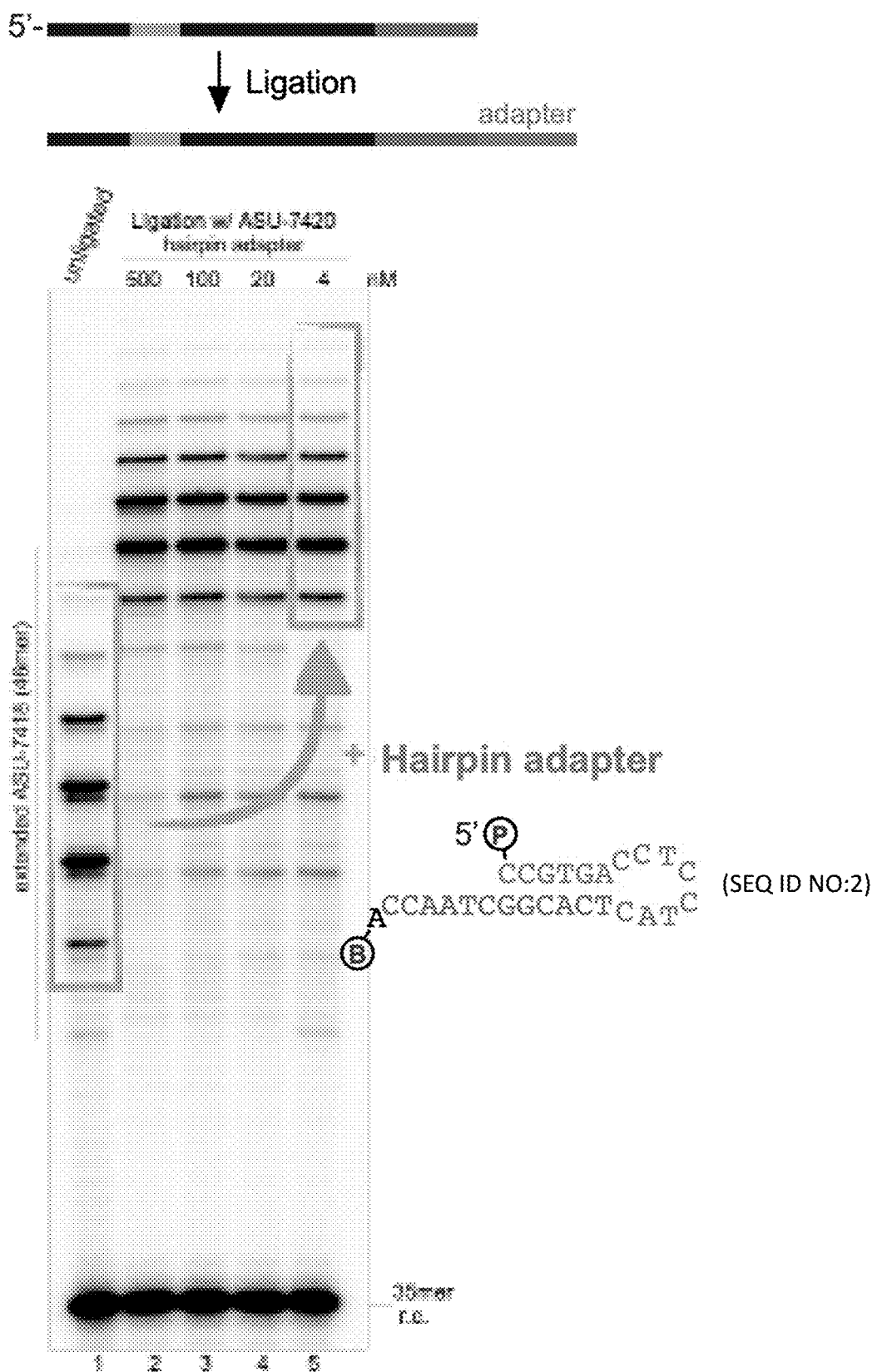
FIG. 5 shows the optimization of ligation reaction conditions for the hairpin adapter ASU-7420 (SEQ ID NO:2). The telomerase-extended DNA products were ligated with different concentrations of the hairpin adapter (lanes 2-5) or without the adapter (lane 1).

To prepare the purified DNA products for next-generation sequencing, they were ligated to a specifically designed hairpin adapter (10 nM) in a 10 µl T4 DNA ligase reaction at 30° C. for 1 hour (FIG. 4). The hairpin adapter contains a 5'-phosphate for ligation and a 3'-biotin-triethyleneglycol (TEG) spacer for affinity purification. The 3'-overhang of the adapter hybridizes specifically with the 3'-end of telomerase-extended DNA products. Importantly, the hairpin structure of this adapter serves to increase its specificity, preventing its binding to residual primer and non-specifically extended DNA products, and thereby enabling the purification of telomerase-extended DNA products only (FIG. 4). The minimal concentration of the hairpin adapter was experimentally determined to be 10 nM (FIG. 5). Additionally, it was determined that the length of the 3'-overhang of the hairpin adapter should be at least six nucleotides (FIG. 6).

After ligation, the adapter-ligated DNA products were affinity purified using 4 µl of Dynabeads MyOne Streptavidin-C1 beads diluted in 40 µl H2O with gentle rotation at room temperature for 30 min, washed twice with 75 µl $H_2O$ at 50° C. for 1 min to remove non-specifically bound DNA primers, and eluted in 40 µl 95% formamide buffer at 65° C. for 5 min. The eluted DNA was subjected to phenol chloroform extraction (i.e., to remove proteins) followed by ethanol precipitation.

Conversion of Adapter-Ligated DNA Products to Sequencing-Ready DNA Library

Illumina sequencing adapters were added to both ends of the purified adapter-ligated DNA products by performing PCR using primers that contain the Illumina adapter sequences (FIG. 1). The first step of PCR was performed using a touchdown annealing step (−1° C./min, ranging from 72° C. to 65° C.) to facilitate initial annealing of the reverse primer to the loop sequence in the hairpin adapter. After a sufficient numbers of PCR cycles (98° C. for 15 sec, 66° C. for 30 sec, 72° C. for 30 sec) using Phusion DNA polymerase, the 141-201 bp PCR DNA products were purified using AMPure XP beads (Beckman Coulter), optionally in a 96-well plate format. The minimal number of PCR cycles required to amplify various amounts of purified adapter-ligated DNA products needs to be experimentally determined. Typically, 10-20 cycles are required to generate a sufficient quantity of amplified DNA for the following indexing step.

Figure 7:
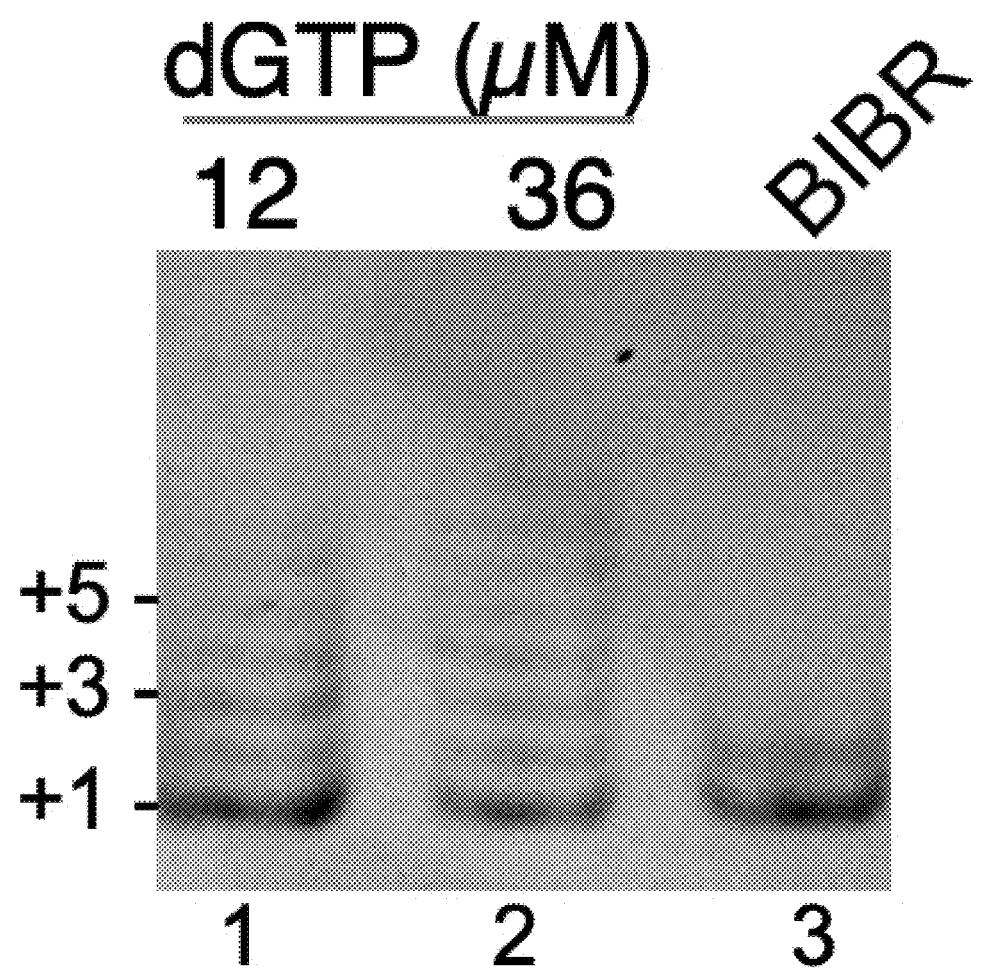
FIG. 7 shows a gel comprising DNA libraries with Illumina adapters. The DNA libraries were amplified from hairpin adapter-ligated DNA products synthesized by telomerase under various conditions (12 or 36 µM dGTP, or in the presence of the telomerase inhibitor BIBR). Notably, the higher dGTP concentration increased the processivity of telomerase, as demonstrated by the addition of a greater number of repeats.

Telomeric DNA products synthesized by telomerase under various conditions can be converted to PCR products that are ready for the final indexing step. In this step, PCR is performed using primers that contain additional Illumina index sequences, generating multiplexed DNA libraries for Illumina next-generation sequencing analysis (FIG. 7). Using this secondary Illumina index system, DNA products from 96 384-well plates may be pooled and sequenced in a single next-generation sequencing reaction, which will make the screening extremely cost-effective. The expected DNA size in the indexed libraries is about 201-261 bp, which can be verified by gel electrophoresis analysis.

Analysis of DNA Products by Illumina Next-Generation Sequencing

By pooling 96 indexed libraries that each contain barcoded DNA products from 768 telomerase primer-extension reactions (i.e., 384 reaction in duplicates), and running them together in a single lane of an Illumina flow cell (which typically produces >300,000,000 reads), each assay allows more than 30,000 compounds to be screened for their ability to affect telomerase activity and processivity. For a sequencing run containing 30,000 reactions, about 10,000 reads should be assigned (i.e., using computational analysis) to each individual reaction, which should be sufficient to distinguish between reactions with various levels of telomerase activity. Thus, this ultra-high-throughput screening method will allow screen U.S. Pat. No. 300,000 compounds in only 10 Illumina DNA sequencing runs.

---

What is claimed:

1. An ultra-high-throughput method for determining telomerase processivity, the method comprising:
   a. incubating a telomerase, a telomeric DNA primer, and dNTPs comprising 5-100 µM dGTP under suitable conditions for telomerase activity, optionally in the presence of an agent, thereby forming telomerase-extended DNA products;
   b. analyzing the telomerase-extended DNA products to determine the processivity of said telomerase;
   c. ligating a hairpin adapter to the telomerase-extended DNA products produced in step (a) prior to step (b) to produce adapter-ligated DNA products; and
   d. amplifying the adapter-ligated DNA products to produce a double-stranded DNA amplicon library, wherein step (b) comprises sequencing the double-stranded DNA amplicon library,
   wherein;
   the telomeric DNA primer comprises:
      a part of a telomeric repeat or at least one telomeric repeat at the 3' end of the telomeric DNA primer; and
      a nucleotide barcode, wherein the nucleotide barcode is selected the group consisting of: ACCCTTG, GCCCTTT, GTGTTCG, TGGGTTT, CCCCTTG, GCCGCTT, GTGTTCT, TGGTCCG, CCCCTTT, GCCGTTT, GTGTTGC, TGGTCGT, CCGCTTG, GCCTCTT, GTGTTGT, TGGTCTG, CCGCTTT, GCCTGTT, GTGTTTG, TGGTCTT, CCGGCTT, GCCTTGG, GTGTTTT, TGGTGCT, CCGGTTG, GCCTTGT, GTTCCCT, TGGTGGT, CCGGTTT, GCCTTTG, GTTCCGG, TGGTGTG, CCGTCTT, GCCTTTT, GTTCCTC, TGGTTCG, CCGTTGT, GCGCCTT, GTTCCTG, TGGTTCT, CCGTTTT, GCGCGTT, GTTCGCG, TGGTTGG, CCTCCGT, GCGCTCT, GTTCGCT, TGGTTGT, CCTCCTT, GCGCTTG, GTTCGGT, TGGTTTC, CCTCGGT, GCGCTTT, GTTCGTC, TGGTTTT, CCTCGTG, GCGGCTT, GTTCGTG, TGTCCCG, CCTCTGT, GCGGGTT, GTTCGTT, TGTCCCT, CCTCTTG, GCGGTGT, GTTCTCT, TGTCCGG, CCTGCTT, GCGGTTT, GTTCTGC, TGTCCTG, CCTGTGT, GCGTCTG, GTTCTGT, TGTCCTT, CCTGTTG, GCGTCTT, GTTCTTC, TGTCGCG, CCTGTTT, GCGTGGT, GTTCTTG, TGTCGCT, CCTTCTG, GCGTGTT, GTTCTTT, TGTCGGT, CCTTGGT, GCGTTCG, GTTGCGG, TGTCGTT, CCTTGTG, GCGTTGT, GTTGCGT, TGTCTCG, CCTTTCG, GCGTTTC, GTTGCTC, TGTCTGG, CCTTTCT, GCGTTTG, GTTGCTG, TGTCTGT, CCTTTGG,
GCGTTTT, GTTGGTC, TGTCTTG, CCTTTGT, GCTCCGT, GTTGGTG, TGTCTTT, CCTTTTG, GCTCCTT, GTTGGTT, TGTGCCT, CCTTTTT, GCTCGCT, GTTGTCG, TGTGCGG, CGCCCTT, GCTCGGT, GTTGTCT, TGTGCGT, CGCCGTT, GCTCGTC, GTTGTGC, TGTGCTC, CGCCTTG, GCTCGTG, GTTGTGG, TGTGCTG, CGCGCTT, GCTCGTT, GTTGTGT, TGTGCTT, CGCGGTT, GCTCTCG, GTTGTTC, TGTGGTG, CGCGTTG, GCTCTCT, GTTGTTG, TGTGGTT, CGCGTTT, GCTCTGG, GTTGTTT, TGTGTGC, CGCTCGT, GCTCTGT, GTTTCCG, TGTGTGG, CGCTCTT, GCTCTTC, GTTTCGT, TGTGTGT, CGCTTCT, GCTCTTG, GTTTCTC, TGTGTTC, CGCTTGT, GCTCTTT, GTTTCTG, TGTGTTG, CGCTTTG, GCTGCTG, GTTTCTT, TGTTCCG, CGCTTTT, GCTGCTT, GTTTGCG, TGTTCCT, CGGCCTT, GCTGGGT, GTTTGCT, TGTTCGC, CGGCGTT, GCTGGTT, GTTTGGC, TGTTCGT, CGGCTTT, GCTGTGT, GTTTGGG, TGTTCTG, CGGGCTT, GCTGTTT, GTTTGGT, TGTTCTT, CGGGTCT, GCTTCCG, GTTTGTC, TGTTGCG, CGGGTTG, GCTTCCT, GTTTGTG, TGTTGGG, CGGGTTT, GCTTCTT, GTTTTCC, TGTTGGT, CGGTCGT, GCTTGCT, GTTTTCG, TGTTGTC, CGGTCTG, GCTTGGT, GTTTTGC, TGTTGTG, CGGTCTT, GCTTGTC, GTTTTGG, TGTTTCG, CGGTGTG, GCTTGTG, GTTTTGT, TGTTTGG, CGGTGTT, GCTTGTT, GTTTTTG, TGTTTGT, CGGTTCG, GCTTTCG, GTTTTTT, TGTTTTG, CGGTTCT, GCTTTGC, TCCCCGG, TTCCCCG, CGGTTGT, GCTTTGT, TCCCCGT, TTCCCGT, CGGTTTT, GCTTTTC, TCCCCTG, TTCCCTG, CGTCCGT, GCTTTTG, TCCCCTT, TTCCCTT, CGTCCTT, GCTTTTT, TCCCGTT, TTCCGCG, CGTCGCT, GGCCCTT, TCCCTTG, TTCCGGG, CGTCGGT, GGCCGTT, TCCCTTT, TTCCGGT, CGTCGTG, GGCCTTT, TCCGCGT, TTCCGTG, CGTCGTT, GGCGCTT, TCCGCTG, TTCCTCG, CGTCTCG, GGCGGTT, TCCGGTG, TTCCTGT, CGTCTTT, GGCGTTT, TCCGGTT, TTCCTTG, CGTGCGT, GGCTCGT, TCCGTCT, TTCCTTT, CGTGCTT, GGCTCTC, TCCGTGT, TTCGCCG, CGTGGGT, GGCTCTT, TCCGTTG, TTCGCCT, CGTGGTG, GGCTGGT, TCCTCGG, TTCGCTC, CGTGTCT, GGCTGTT, TCCTCTT, TTCGCTG, CGTGTGG, GGCTTCG, TCCTCTT, TTCGCTT, CGTGTGT, GGCTTCT, TCCTGTT, TTCGGCT, CGTGTTG, GGCTTGC, TCCTTGG, TTCGGTG, CGTGTTT, GGCTTGG, TCCTTGT, TTCGGTT, CGTTCCT, GGCTTGT, TCCTTTG, TTCGTCG, CGTTCGT, GGCTTTC, TCCTTTT, TTCGTCT, CGTTCTG, GGCTTTG, TCGCCCT, TTCGTGG, CGTTCTT, GGGCTTT, TCGCCTT, TTCGTGT, CGTTGCG, GGGGTCT, TCGCGCT, TTCGTTC, CGTTGGG, GGGGTTG, TCGCGGT, TTCGTTG, CGTTGGT, GGGGTTT, TCGCGTG, TTCGTTT, CGTTGTG, GGGTCTT, TCGCGTT, TTCTCCG, CGTTGTT, GGGTGTT, TCGCTCG, TTCTCCT, CGTTTCG, GGGTTGT, TCGCTCT, TTCTCGG, CGTTTCT, GGGTTTT, TCGCTTG, TTCTCGT, CGTTTGC, GGTCCCT, TCGCTTT, TTCTCTC, CGTTTGG, GGTCCGT, TCGGCGT, TTCTCTG, CGTTTGT, GGTCCTC, TCGGCTT, TTCTCTT, CGTTTTC, GGTCCTG, TCGGTCT, TTCTGCT, CGTTTTG, GGTCCTT, TCGGTTC, TTCTGGG, CGTTTTT, GGTCGCT, TCGGTTG, TTCTGGT, CTCCCTT, GGTCGTC, TCGGTTT, TTCTGTG, CTCCGCT, GGTCGTT, TCGTCCG, TTCTTGC, CTCCGGT, GGTCTCC, TCGTCGT, TTCTTGG, CTCCGTG, GGTCTCT, TCGTCTG, TTCTTTG, CTCCGTT, GGTCTGT, TCGTCTT, TTCTTTT, CTCCTCG, GGTCTTC, TCGTGGG, TTGCCCG, CTCCTTG, GGTCTTG, TCGTGGT, TTGCCGT, CTCCTTT, GGTCTTT, TCGTGTG, TTGCCTG, CTCGCGT, GGTGCGT, TCGTGTT, TTGCCTT, CTCGCTG, GGTGCTC, TCGTTCG, TTGCGCG, CTCGCTT, GGTGCTT, TCGTTGG, TTGCGCT, CTCGGGT, GGTGGCT, TCGTTGT, TTGCGGG, CTCGTCT, GGTGTCT, TCGTTTG, TTGCGGT, CTCGTGG, GGTGTGT, TCGTTTT, TTGCGTG, CTCGTGT, GGTGTTG, TCTCCCG, TTGCTCT, CTCGTTG, GGTGTTT, TCTCCGG, TTGCTGT, CTCGTTT, GGTTCCG, TCTCCGT, TTGCTTC, CTCTCGG, GGTTCCT, TCTCCTG, TTGCTTG, CTCTCGT, GGTTCGC, TCTCCTT, TTGCTTT, CTCTCTG, GGTTCGG, TCTCGCT, TTGGCCG, CTCTCTT, GGTTCTC, TCTCGGT, TTGGCCT, CTCTTCG, GGTTCTG, TCTCGTC, TTGGCGT, CTCTTCT, GGTTGCT, TCTCGTG, TTGGCTT, CTCTTGG, GGTTGGG, TCTCGTT, TTGGGCT, CTCTTGT, GGTTGTC, TCTCTCT, TTGGGTT, CTCTTTG, GGTTGTG, TCTCTGG, TTGGTGG, CTCTTTT, GGTTGTT, TCTCTGT, TTGGTGT, CTGCCGT, GGTTTCC, TCTCTTG, TTGGTTC, CTGCGGT, GGTTTCG, TCTCTTT, TTGGTTG, CTGCGTG, GGTTTCT, TCTGCCT, TTGGTTT, CTGCGTT, GGTTTGG, TCTGCGT, TTGTCCG, CTGCTCT, GGTTTGT, TCTGCTG, TTGTCCT, CTGCTTG, GGTTTTC, TCTGCTT, TTGTCGT, CTGCTTT, GGTTTTG, TCTGGTG, TTGTCTC, CTGGCGT, GGTTTTT, TCTGGTT, TTGTCTG, CTGGGTG, GTCCCCT, TCTGTCT, TTGTCTT, CTGGGTT, GTCCCGT, TCTGTGG, TTGTGCG, CTGGTCT, GTCCCTT, TCTGTGT, TTGTGCT, CTGGTGT, GTCCGGT, TCTGTTG, TTGTGGG, CTGGTTG, GTCCGTG, TCTGTTT, TTGTGGT, CTGGTTT, GTCCGTT, TCTTCGG, TTGTGTC, CTGTCCG, GTCCTCG, TCTTCTG, TTGTGTG, CTGTCCT, GTCCTCT, TCTTCTT, TTGTGTT, CTGTCGG, GTCCTGT, TCTTGCG, TTGTTCG, CTGTCTG, GTCCTTC, TCTTGCT, TTGTTGC, CTGTCTT, GTCCTTG, TCTTGGG, TTGTTGT, CTGTGCT, GTCCTTT, TCTTGGT, TTGTTTT, CTGTGGT, GTCGCGT, TCTTGTT, TTTCCCG, CTGTGTT, GTCGCTG, TCTTTCG, TTTCCCT, CTGTTCG, GTCGCTT, TCTTTGG, TTTCCGC, CTGTTGG, GTCGGCT, TCTTTGT, TTTCCGG, CTGTTGT, GTCGGTG, TCTTTTG, TTTCCTG, CTGTTTC, GTCGGTT, TGCCCCT, TTTCCTT, CTGTTTG, GTCGTCT, TGCCCGT, TTTCGCG, CTTCCCT, GTCGTGT, TGCCCTT, TTTCGCT, CTTCCGT, GTCGTTG, TGCCGCT, TTTCGGC, CTTCCTT, GTCGTTT, TGCCGTG, TTTCGGG, CTTCGCG, GTCTCCG, TGCCTGT, TTTCGGT, CTTCGGG, GTCTCCT, TGCGCGT, TTTCGTC, CTTCGGT, GTCTCGC, TGCGCTG, TTTCGTT, CTTCGTG, GTCTCGG, TGCGCTT, TTTCTCT, CTTCGTT, GTCTCGT, TGCGGGT, TTTCTGC, CTTCTCG, GTCTCTC, TGCGGTT, TTTCTGG, CTTCTGG, GTCTCTG, TGCGTCT, TTTCTTG, CTTCTGT, GTCTCTT, TGCGTGG, TTTGCCG, CTTCTTC, GTCTGCT, TGCGTGT, TTTGCCT, CTTCTTG, GTCTGGT, TGCGTTG, TTTGCGC, CTTCTTT, GTCTGTT, TGCGTTT, TTTGCGG, CTTGCCT, GTCTTGC, TGCTCCG, TTTGCGT, CTTGCTG, GTCTTGT, TGCTCGC, TTTGCTC, CTTGCTT, GTCTTTC, TGCTCGG, TTTGCTG, CTTGGCT, GTCTTTG, TGCTCGT, TTTGCTT, CTTGGGT, GTCTTTT, TGCTCTG, TTTGGCG, CTTGGGT, GTGCCCT, TGCTCTT, TTTGGGT, CTTGTCG, GTGCCTT, TGCTGCT, TTTGGTG, CTTGTCT, GTGCGCT, TGCTGGT, TTTGGTT, CTTGTGG, GTGCGGT, TGCTGTG, TTTGTCG, CTTGTGT, GTGCGTT, TGCTGTT, TTTGTCT, CTTGTTG, GTGCTCG, TGCTTCG, TTTGTGG, CTTGTTT, GTGCTCT, TGCTTGC, TTTGTGT, CTTTCCG, GTGCTGT, TGCTTGG, TTTGTTG, CTTTCGG, GTGCTTC, TGCTTTC, TTTTCCG, CTTTCGT, GTGCTTG, TGGCCTT, TTTTCCT, CTTTCTC, GTGGGTC, TGGCGCT, TTTTCGC, CTTTCTG, GTGGTCG, TGGCGGT, TTTTCGG, CTTTCTT, GTGGTCT, TGGCGTT, TTTTCGT, CTTTGCG, GTGGTTC, TGGCTCG, TTTTCTG, CTTTGCT, GTGGTTG, TGGCTTC, TTTTCTT, CTTTGGT, GTGTCCG, TGGCTTG, TTTTGCG, CTTTGTG, GTGTCCT, TGGCTTT, TTTTGCT, CTTTGTT, GTGTCGG, TGGGCCT, TTTTGGC, CTTTTCG, GTGTCGT, TGGGCTG, TTTTGGG, CTTTTGC, GTGTCTC, TGGGCTT, TTTTGGT, CTTTTGG, GTGTCTG, TGGGGCT, TTTTGTG, CTTTTGT, GTGTCTT, TGGGGTT, TTTTTCG, CTTTTTG, GTGTGCT, TGGGTCT, TTTTTGC, CTTTTTT, GTGTGGT, TGGGTGT, TTTTTGG, GCCCGTT, GTGTGTC, TGGGTTC, TTTTTGT, GCCCTGT, GTGTGTT, TGGGTTG, and TTTTTTG; and the hairpin adapter specifically binds to the telomerase-extended DNA products but does not bind to the telomeric DNA primer, and wherein the hairpin adapter comprises:
    a sequence that is complementary to the 3' end of the telomerase-extended DNA products;
    a 5' phosphate to allow for ligation with the telomerase-extended DNA products;
    a purification moiety;
    a PCR primer binding site;
    a stem-loop structure comprising a double-stranded stem and a single-stranded loop; and
    a single-stranded 3'-overhang,
wherein the PCR primer binding site is contained within the single-stranded loop, and wherein the sequence that is complementary to the 3' end of the telomerase-extended DNA products is located within the single-stranded 3'-overhang.

2. The method of claim 1, wherein the single-stranded 3'-overhang is at least 6 nucleotides in length.

3. The method of claim 1, wherein the concentration of the hairpin adaptor is at least 10 nM.

4. The method of claim 1, wherein the method further comprises affinity purifying the telomerase-extended DNA products using the purification moiety of the hairpin adaptor after the telomerase-extended DNA products are ligated to the hairpin adaptor.

5. The method of claim 1, wherein the nucleotide barcode is flanked by sequences that form a stem, such that the nucleotide barcode resides within a loop region of a stem-loop structure.

6. The method of claim 1, wherein the incubating in step (a) is performed for 20-30 minutes at room temperature.

7. The method of claim 1, wherein the method further comprises adding sequencing adapters to the ends of the telomerase-extended DNA products prior to step (b).

8. The method of claim 1, wherein the telomerase-extended DNA products are pooled from at least 300 reactions and sequenced in the same sequencing reaction.

9. The method of claim 8, wherein the telomerase-extended DNA products are pooled from at least 30,000 reactions and sequenced in the same sequencing reaction.

10. The method of claim 1, wherein the sequence that complementary to the 3' end of telomerase-extended DNA product comprises sequence selected from the group consisting of: CCAATC (3' to 5'); CAATCC (3' to 5'); and AATCCC (3' to 5').

11. The method of claim 10, wherein the single-stranded 3'-overhang is 6-7 nucleotides in length.

* * * * *

SEQUENCE LISTING

<160> NUMBER OF SEQ ID NOS: 10

<210> SEQ ID NO 1
<211> LENGTH: 49
<212> TYPE: DNA
<213> ORGANISM: Artificial Sequence
<220> FEATURE:
<223> OTHER INFORMATION: Synthetic - generic telomeric DNA primer
<220> FEATURE:
<221> NAME/KEY: misc_feature
<222> LOCATION: (23)..(28)
<223> OTHER INFORMATION: Barcode sequence; N is G, C, A, or T

<400> SEQUENCE: 1
cagggatagc atgttgcctc gtnnnnnntc gaggttgctg ggagaggtt            49

<210> SEQ ID NO 2
<211> LENGTH: 27
<212> TYPE: DNA
<213> ORGANISM: Artificial Sequence
<220> FEATURE:
<223> OTHER INFORMATION: Synthetic - hairpin adapter ASU-7420

<400> SEQUENCE: 2
ccgtgacctc ctactcacgg ctaacca                                    27

<210> SEQ ID NO 3

```
<211> LENGTH: 25
<212> TYPE: DNA
<213> ORGANISM: Artificial Sequence
<220> FEATURE:
<223> OTHER INFORMATION: Synthetic - hairpin adapter ASU-7540

<400> SEQUENCE: 3
ccgtgacctc ctactcacgg ctaac                                         25

<210> SEQ ID NO 4
<211> LENGTH: 24
<212> TYPE: DNA
<213> ORGANISM: Artificial Sequence
<220> FEATURE:
<223> OTHER INFORMATION: Synthetic - hairpin adapter ASU-7541

<400> SEQUENCE: 4
ccgtgacctc ctactcacgg ctaa                                          24

<210> SEQ ID NO 5
<211> LENGTH: 11
<212> TYPE: RNA
<213> ORGANISM: Artificial Sequence
<220> FEATURE:
<223> OTHER INFORMATION: Synthetic - telomerase RNA template sequence

<400> SEQUENCE: 5
cuaacccuaa c                                                        11

<210> SEQ ID NO 6
<211> LENGTH: 12
<212> TYPE: DNA
<213> ORGANISM: Artificial Sequence
<220> FEATURE:
<223> OTHER INFORMATION: Synthetic - 3' end of a telomerase-extended DNA
      product comprising 2 repeats (Fig. 2A)

<400> SEQUENCE: 6
ggttagggtt ag                                                       12

<210> SEQ ID NO 7
<211> LENGTH: 18
<212> TYPE: DNA
<213> ORGANISM: Artificial Sequence
<220> FEATURE:
<223> OTHER INFORMATION: Synthetic - 3' end of a telomerase-extended DNA
      product comprising 3 repeats (Fig. 2A)

<400> SEQUENCE: 7
ggttagggtt agggttag                                                 18

<210> SEQ ID NO 8
<211> LENGTH: 33
<212> TYPE: DNA
<213> ORGANISM: Artificial Sequence
<220> FEATURE:
<223> OTHER INFORMATION: Synthetic - 3' end of a telomerase-extended DNA
      product ligated to hairpin adapter ASU-7420 (Fig. 4)

<400> SEQUENCE: 8
ggttagccgt gacctcctac tcacggctaa cca                                33

<210> SEQ ID NO 9
<211> LENGTH: 46
<212> TYPE: DNA
<213> ORGANISM: Artificial Sequence
<220> FEATURE:
```

<223> OTHER INFORMATION: Synthetic - primer ASU-7418

<400> SEQUENCE: 9
ggatagcatg ttgcctcgtt ctcttctcga ggttgctggg agagtt       46

<210> SEQ ID NO 10
<211> LENGTH: 46
<212> TYPE: DNA
<213> ORGANISM: Artificial Sequence
<220> FEATURE:
<223> OTHER INFORMATION: Synthetic - primer ASU-7419

<400> SEQUENCE: 10
ggatagcatg ttgcctcgtt ctcttctcga ggttagggtt agggtt       46